US008278429B2

(12) United States Patent
Park et al.

(10) Patent No.: US 8,278,429 B2
(45) Date of Patent: Oct. 2, 2012

(54) OLIGONUCLEOTIDE AMPLIFICATION PRIMERS FOR TARGETING ONCOGENIC HPV

(75) Inventors: Daniel J. Park, Heathmont (AU); Zaheer Khan, Manukau (NZ); Karl F. Poetter, Northcote (AU)

(73) Assignee: Genera Biosystems Limited, Scoresby, Victoria (AU)

( * ) Notice: Subject to any disclaimer, the term of this patent is extended or adjusted under 35 U.S.C. 154(b) by 61 days.

(21) Appl. No.: 12/594,817

(22) PCT Filed: Apr. 4, 2008

(86) PCT No.: PCT/US2008/004441
§ 371 (c)(1),
(2), (4) Date: Apr. 30, 2010

(87) PCT Pub. No.: WO2008/124091
PCT Pub. Date: Oct. 16, 2008

(65) Prior Publication Data
US 2010/0279888 A1 Nov. 4, 2010

Related U.S. Application Data

(60) Provisional application No. 60/910,381, filed on Apr. 5, 2007, provisional application No. 60/910,373, filed on Apr. 5, 2007.

(51) Int. Cl.
*C07H 21/02* (2006.01)
*C07H 21/04* (2006.01)
*C12Q 1/68* (2006.01)
*C12P 19/34* (2006.01)

(52) U.S. Cl. ....... 536/23.1; 435/6.1; 435/91.2; 536/23.5

(58) Field of Classification Search .......................... None
See application file for complete search history.

(56) References Cited

U.S. PATENT DOCUMENTS

| 4,983,728 | A | 1/1991 | Herzog et al. |
|---|---|---|---|
| 5,346,811 | A | 9/1994 | Galindo-Castro et al. |
| 5,364,758 | A | 11/1994 | Meijer et al. |
| 5,411,857 | A | 5/1995 | Beaudenon et al. |
| 5,484,699 | A | 1/1996 | Bouma et al. |
| 5,527,898 | A | 6/1996 | Bauer et al. |
| 5,580,970 | A | 12/1996 | Hendricks et al. |
| 5,643,715 | A | 7/1997 | Lancaster |
| 5,656,423 | A | 8/1997 | Orth et al. |
| 5,705,627 | A | 1/1998 | Manos et al. |
| 5,712,092 | A | 1/1998 | Orth et al. |
| 5,723,296 | A | 3/1998 | Nycz et al. |
| 5,876,922 | A | 3/1999 | Orth et al. |
| 5,958,674 | A | 9/1999 | Beaudenon et al. |
| 5,981,171 | A | 11/1999 | Kuhns |
| 5,981,180 | A | 11/1999 | Chandler et al. |
| 6,265,154 | B1 | 7/2001 | Kroeger et al. |
| 6,312,928 | B1 | 11/2001 | Van Gemen et al. |
| 6,352,825 | B1 | 3/2002 | Meijer et al. |
| 6,482,588 | B1 | 11/2002 | Van Doorn et al. |
| 6,511,805 | B1 | 1/2003 | Gocke et al. |
| 6,583,278 | B1 | 6/2003 | Carter |
| 7,063,963 | B2 | 6/2006 | Cole et al. |
| 7,183,053 | B2 | 2/2007 | Gocke et al. |
| 2002/0081617 | A1 | 6/2002 | Buranda et al. |
| 2003/0224385 | A1 | 12/2003 | Pihan |

FOREIGN PATENT DOCUMENTS

| EP | 746627 B1 * | 8/2002 |
|---|---|---|
| WO | WO 03/019143 | 3/2003 |
| WO | WO 2006/060872 A1 | 6/2006 |

OTHER PUBLICATIONS

GenBank AF043287, Apr. 2, 1998, from www.ncbi.nlm.nih.gov, pp. 1-2.*
Heinzel P.A. et al. Journal of Clinical Microbiology, Jul. 1995, p. 1746-1754.*
Baldwin et al., "Human papillomavirus infection in men attending a sexually transmitted disease clinic," Journal of Infectious Diseases, 2003, vol. 187, pp. 1064-1070.
Bleeker et al., "Concordance of specific human papillomavirus types in sex partners is more prevalent than would be expected by chance and is associated with increased viral loads," Clinical Infectious Diseases, 2005, vol. 41, pp. 612-620.
Bosch et al., "The aetiology of cervical cancer," NHSCSP Publication No. 22, Sep. 2005.
Brown et al., "Distribution of human papillomavirus types in cervicovaginal washings from women evaluated in a sexually transmitted disease clinic," Sexually Transmitted Diseases, Dec. 2002, pp. 763-768.
Cavuslu et al., "Analytic sensitivities of hybrid-capture, consensus and type-specific polymerase chain reactions for the detection of human papillomavirus type 16 DNA," Journal of Medical Virology, 1996, vol. 49, pp. 319-324.
Evans et al., "Touchdown general primer (GP5+/GP6+) PCR and optimized sample DNA concentration support the sensitive detection of human papillomavirus," BMC Clinical Pathology, 2005, vol. 10:5, pp. 1-14.
Gravitt et al., "Improved amplification of genital human papillomaviruses," Journal of Clinical Microbiology, Jan. 2000, vol. 38, No. 1, pp. 357-361.

(Continued)

*Primary Examiner* — Stephen Kapushoc
(74) *Attorney, Agent, or Firm* — Knobbe, Martens, Olson & Bear, LLP

(57) ABSTRACT

The present invention relates generally to the field of diagnostic and detection assays. More particularly, the present invention provides methods and reagents including biochips for detecting the presence of, or distinguishing between, one or more analytes in a sample.

24 Claims, 8 Drawing Sheets

OTHER PUBLICATIONS

Gravitt et al., "A comparison between real-time polymerase chain reaction and hybrid capture 2 for human papillomavirus DNA quantitation," Cancer Epidemiology, Biomarkers & Prevention, Jun. 2003, vol. 12, pp. 477-484.

Hart et al., "Novel method for detection, typing, and quantification of human papillomaviruses in clinical samples," Journal of Clinical Microbiology, Sep. 2001, vol. 39, No. 9, pp. 3204-3212.

Jacobs et al., "A quantitative polymerase chain reaction-enzyme immunoassay for accurate measurements of human papillomavirus type 16 DNA levels in cervical scrapings," British Journal of Cancer, 1999, vol. 81(1), pp. 114-121.

Jastania et al., "Characteristics of Apparently False-Negative Digene Hybrid Capture 2 High-Risk HPV DNA Testing," American Journal of Clinical Pathology, 2006, vol. 125(2), pp. 223-228.

Lai et al., "Differential viral loads of human papillomavirus 16 and 58 infections in the spectrum of cervical carcinogenesis," International Journal of Gynecological Cancer, 2006, vol. 16, pp. 730-735.

Lapin et al., "Oncologic colpocytology collected in the public health and reference services in the diagnostic of the severity of intraepithelial cervical lesion," Journal of Public Health, Apr. 2000, vol. 34, No. 2, pp. 120-125.

Lorincz et al., "Viral load of human papillomavirus and risk of CIN3 or cervical cancer," The Lancet, Jul. 20, 2002, vol. 360, pp. 228-229.

McQueen et al., "Using a quality control approach to define an 'adequately cellular' liquid-based cervical cytology specimen," Cytopathology, Aug. 2006, vol. 17, issue 4, pp. 168-174.

Minkoff et al., "The effect of highly active antiretroviral therapy on cervical cytologic changes associated with oncogenic HPV among HIV-infected women," AIDS 2001, vol. 15, No. 16, pp. 2157-2164.

Quint et al., "Results of the first World Health Organization international collaborative study of detection of human papillomavirus DNA," Journal of Clinical Microbiology, Feb. 2006, vol. 44, No. 2, pp. 571-579.

Ruffin et al., "Low-dose topical delivery of all-trans retinoic acid for cervical intraepithelial neoplasia II and III," Cancer Epidemiology, Biomarkers & Prevention, Dec. 2004, vol. 13(12), pp. 2148-2152.

Sherman et al., "Determinants of human papillomavirus load among women with histological cervical intraepithelial neoplasia 3: dominant impact of surrounding low-grade lesions," Cancer Epidemiology, Biomarkers & Prevention, Oct. 2003, vol. 12, pp. 1038-1044.

Stevens et al., "Assessment of MagNA pure LC extraction system for detection of human papillomavirus (HPV) DNA in PreservCyt samples by the Roche AMPLICOR and Linear Array HPV tests," Journal of Clinical Microbiology, Jul. 2006, vol. 44, No. 7, pp. 2428-2435.

Swan et al., "A sensitive, type-specific, fluorogenic probe assay for detection of human papillomavirus DNA," Journal of Clinical Microbiology, Apr. 1997, vol. 35, No. 4, pp. 885-891.

Swan et al., "Human papillomavirus (HPV) DNA copy number is dependant on grade of cervical disease and HPV type," Journal of Clinical Microbiology, Apr. 1999, vol. 37, No. 4, pp. 1030-1034.

Tapsall et al., "Applications of molecular testing in clinical laboratories for the diagnosis and control of gonorrhea," Future Microbiology, 2006, vol. 1(3), pp. 1-7.

Tsai et al., "Association between quantitative high-risk human papillomavirus DNA load and cervical intraepithelial neoplasm risk," Cancer Epidemiology, Biomarkers & Prevention, Nov. 2005, vol. 14(11), pp. 2544-2549.

Van Duin et al., "Human papillomavirus 16 load in normal and abnormal cervical scrapes: An indicator of CIN II/III and viral clearance," International Journal of Cancer, 2002, vol. 98, pp. 590-595.

Venturoli et al., "Evaluation of immunoassays for the detection and typing of PCR amplified human papillomavirus DNA," Journal of Clinical Pathology, 1998, vol. 51, pp. 143-148.

Wallboomers et al., "Human papillomavirus is a necessary cause of invasive cervical cancer worldwide," Journal of Pathology, 1999, vol. 189, pp. 12-19.

Weissenborn et al., "Oncogenic human papillomavirus DNA loads in human immunodeficiency virus-positive women with high-grade cervical lesions are strongly elevated," Journal of Clinical Microbiology, Jun. 2003, vol. 41, No. 6, pp. 2763-2767.

Ylitalo et al., "Consistent high viral load of human papillomavirus 16 and risk of cervical carcinoma in situ: a nested case-control study," The Lancet, Jun. 24, 2000, vol. 355, pp. 2194-2198.

Zerbini et al., "Distribution and viral load of type specific HPVs in different cervical lesions as detected by PCR-ELISA," Journal of Clinical Pathology, 2001, vol. 54, pp. 377-380.

\* cited by examiner

FIGURE 5

|  | TMR Level | | | |
|---|---|---|---|---|
|  | 0 | 100% | 20% | 4% |
| 6.8 um | $X_1$ | $X_2$ | $X_3$ | $X_4$ |
| 5.6 um | $X_5$ | $X_6$ | $X_7$ | $X_8$ |
| 5.0 um | $X_{11}$ | $X_9$ | $X_{10}$ | |
| 4.1 um | $X_{13}$ | $X_{12}$ | | |
| 3.5 um | Z | $X_{14}$ | | |
| 3.0 um | $X_{LR}$ | Y | | |

FIGURE 6

| Strain | Bead size | TMR ratio |
|---|---|---|
| 6 | 3.0um | High TMR |
| 11 | 3.0um | No TMR |
| 16 | 5.0um | Medium TMR |
| 18 | 5.0um | High TMR |
| 31 | 4.1um | No TMR |
| 33 | 5.0um | No TMR |
| 35 | 5.6um | No TMR |
| 39 | 3.5um | Medium TMR |
| 45 | 3.5um | High TMR |
| 51 | 4.1um | Medium TMR |
| 52 | 6.8um | Medium TMR |
| 56 | 4.1um | High TMR |
| 58 | 6.8um | High TMR |
| 59 | 5.6um | High TMR |
| 66 | 5.6um | Medium TMR |
| 68 | 6.8um | No TMR |
| MLC1 control | 5.6um | No TMR |

Sensitivity Testing for Probe Methodology

OLIGONUCLEOTIDE AMPLIFICATION PRIMERS FOR TARGETING ONCOGENIC HPV

CROSS REFERENCE TO RELATED APPLICATION

This application is a U.S. National Phase of International Application No.: PCT/US2008/004441, filed Apr. 4, 2008, designating the U.S. and published in English on Oct. 16, 2008 as WO 2008/124091, which claims the benefit of U.S. Provisional Application No. 60/910,381, filed Apr. 5, 2007 and U.S. Provisional Application No. 60/910,373, filed Apr. 5, 2007.

FIELD OF THE INVENTION

The present invention relates generally to the field of diagnostic and detection assays. More particularly, the present invention provides methods, and reagents including biochips for detecting the presence of, or distinguishing between, one or more analytes in a sample.

BACKGROUND OF THE INVENTION

Bibliographical details of references provided in the subject specification are listed at the end of the specification.

Reference to any prior art in this specification is not, and should not be taken as, an acknowledgement or any form of suggestion that this prior art forms part of the common general knowledge in any country.

The need for rapid and reliable screening methods for detecting multiple analytes in a single assay is vital not only in the fields of clinical diagnosis, but also for use in screening, for example, for environmental toxins and drug screening.

One such area which is desperately in need of improved screening methods and reagents is in the field of infectious diseases. For example, a conservative estimate of the world use of diagnostic tests for sexually transmitted diseases, such as Human Papilloma Virus (HPV), is approximately 20,000,000 tests per year.

Many of the existing tests for screening for the causes of infectious diseases are time consuming, labor intensive, expensive, often specific for only one specific pathogen and/or cannot differentiate between different strains of pathogens.

HPV is the main causative pathogen for cervical cancer. However, the HPV taxon comprises many "strains" of the pathogen, only some of which are associated with the development of cervical cancer and other carcinomas. Accordingly, the strains of HPV are typically classified as either "high risk" strains, including the 13 strains which account for roughly 98% of cervical cases, or "low risk" strains which are not typically associated with the development of cervical cancer.

Currently, cervical cancer is detected by a Pap smear. In this technique, cells are collected from the cervix by scraping or washing. These cells are then placed on a glass microscope slide to produce the "smear". A pathologist then examines the slide, looking for aberrant cells. The Pap smear, however, is a somewhat unsatisfactory assay for unequivocally determining cervical cancer risk, as the technique has a false negative rate of approximately 20% and the technique cannot distinguish "high risk" and "low risk" taxon.

Many of the reagents and/or methods for detection of HPV suffer from high associated costs and/or consume significant amounts of time to complete. More rapid and/or simplified analyses having lower overall costs and easier application are needed. The present invention is directed to these and other important ends.

SUMMARY OF THE INVENTION

The present invention provides assays which enable the detection of one or more analytes and/or which differentiate between members within a class of analytes. In particular, multiplexing analysis based on the properties of the analytes and of the assay components is employed to identify or distinguish between analytes.

Accordingly, certain aspects of the present invention provides beadsets for detecting one or more analytes and/or for differentiating between two or more members within a class of analytes, wherein the beadset comprises a plurality of families or subsets of beads wherein:
 (a) the beads of each subset are homogeneous with respect to size;
 (b) the beads within each subset are coupled to a reactant that will specifically react with a given analyte of interest in a sample to be tested;
 (c) the reactant on each bead is labelled with the same label with each subset of beads having a different fluorescent intensity to create a heterogeneous mixture of subsets of beads based on fluorescent intensity; and
 (d) at least two subsets of beads are mixed together to produce a beadset, wherein the subset identity and therefore the reactant to which the bead has been coupled is identifiable by flow cytometry based on size, fluorescent intensity and analyte discrimination.

In other aspects, the present invention contemplates methods for detecting and/or differentiating between two or more analytes in a sample, comprising the steps of:
 (a) contacting the sample with a beadset specific for the analytes of interest;
 (b) incubating said beadset with said sample for a time and under conditions sufficient to allow said analyte(s) in said sample to react specifically with a reactant on a bead within said beadset; and
 (c) detecting and/or differentiating analytes in the sample which are bound to a reactant on said bead.

In some other aspects, the reactants may be labelled with one or more fluorochromes that further allow differentiation between members within a class of analytes. In certain preferred aspects, the present invention provides methods and beadsets which are able to detect and/or distinguish between analytes within a biological sample, wherein the analytes are specific for an infectious pathogen.

Biological samples contemplated herein include blood, serum, saliva, faeces, urine, tissue fluid, semen, exudate, pus, and respiratory fluid and mucus and swabs from topical sores, cancers and lesions.

The term "pathogen" refers to a microorganism or virus which infects or colonizes a sample. Exemplary pathogens include viruses, bacteria, fungi and eukaryotic microorganisms. A virus includes a Lentivirus (e.g. AIDS virus, HIV-I, HIV-II, HTLV-IV), Retrovirus and avian flu virus. In some preferred embodiments, "pathogen" includes a microorganism or virus which infects a multicellular organism such as an animal or plant. Accordingly, in some embodiments, the analyte may be regarded as an animal or plant pathogen. However, the present invention encompasses the detection and/or differentiation of non-pathogenic entities which colonize multicellular organisms such as symbionts, endophytes, gastrointestinal colonists, and the like. The methods of the present invention are also applicable to the detection of analytes in a sample which are indicative of the presence of therapeutic agents or substances of abuse. The methods and reagents of the present invention may also be used in the detection of an analyte in a sample which is not derived from a biological sample isolated from an animal or a plant. As such, the reagents and methods of the present invention also extend to the detection of one or more analytes and/or differentiation between analytes in environmental samples, including air, water and soil samples, including extraterrestrial soil, dust or like samples, industrial samples and the like, in addition to the biological samples listed above.

In certain embodiments, the present invention provides for diagnostic methods and reagents for HPV in human subjects and is able to detect and differentiate between different strains in order to distinguish "high risk" HPV taxon from "low risk" HPV taxon. Accordingly, in some preferred embodiments, the present invention provides beadsets which are able to distinguish between pluralities of different HPV strains. As such, in one aspect, the analytes are specific for a plurality of HPV taxons and the methods and/or reagents are specific for the detection of nucleic acid or antigens or antibodies which are specific for the plurality of HPV taxons.

Even more preferred, nucleic acid primers or probes capable of binding to a strain-specific portion of an HPV genome are immobilized onto beads in each bead subset. Primers directed to conserved regions within an HPV genome flanking a strain-specific region are then used to amplify the HPV genome. Families of beads or subsets of beads, each for any one strain of HPV are then used to detect or distinguish the HPV strain.

Other aspects of the present invention are directed to beadsets for detecting one or more strains of HPV and/or for differentiating between two or more strains of HPV, wherein the beadset comprises a plurality of families or subsets of beads wherein:

(a) the beads of each subset are homogeneous with respect to size;

(b) the beads within each subset are coupled to a nucleic acid capture probe which is capable of binding to a HPV strain-specific region of an HPV genome or, optionally, a control nucleic acid sequence;

(c) the capture probe on each bead is labelled with the same label with each subset of beads having a different fluorescent intensity to create a heterogeneous mixture of beads based on fluorescent intensity; and (d) at least two subsets of beads are mixed together to produce a beadset, wherein the subset identity and therefore the strain of HPV is identifiable by flow cytometry based on size, fluorescent intensity and sequence discrimination.

Other aspects of the present invention contemplate methods for detecting and/or differentiating between two or more HPV strains in a sample, comprising the steps of (a) contacting the sample with a beadset comprising a plurality of families or subsets of beads wherein:

(i) the beads of each subset are homogeneous with respect to size;

(ii) the beads within each subset are coupled to a nucleic acid capture probe which is capable of binding to a HPV strain-specific region of an HPV genome or, optionally, a control nucleic acid sequence;

(iii) the capture probe on each bead is labelled with the same label with each subset of beads having a different fluorescent intensity to create a heterogeneous mixture of beads based on fluorescent intensity; and (iv) at least two subsets of beads are mixed together to produce a beadset, wherein the subset identity and therefore the strain of HPV is identifiable by flow cytometry based on size, intensity and sequence discrimination;

(b) incubating said beadset with said sample for a time and under conditions sufficient to allow said probes to bind to the HPV genome amplified to generate a replicon comprising a strain-specific region;

(c) detecting and/or differentiating the amplicons generated in the sample which are bound to said beads to thereby identify or distinguish between the two or more HPV strains.

In some preferred aspects, the beads within the beadsets are distinguishable on the basis of size, the level of fluorescent intensity, the type of fluorochrome and the reactant which is capable of reacting with a specific analyte.

In other aspects, the present invention is directed to beadsets for detecting a strain of HPV and/or for differentiating between two or more strains of HPV, wherein the beadset comprises a plurality of families or a plurality of subsets of beads having:

(a) at least two subsets of beads, wherein each subset of beads is physiochemically distinguishable from any other bead subset based on at least size; or (b) at least one subset of beads having at least two families, wherein the beads in a bead subset are homogeneous in size with respect to each other, and are physiochemically distinguishable into two or more families of beads based on the level of labelling each contains, or (c) a combination of said families of beads and said subsets of beads; and wherein:

the beads within each bead family of a subset are each coupled to an optionally-labelled nucleic acid capture probe capable of binding to a HPV strain-specific region of an HPV genome or, optionally, to at least one of a control nucleic acid sequence, provided that any nucleic acid capture probe or control nucleic acid sequence is labelled with the same label as other labelled capture probes or control nucleic acid sequence in the bead subset, and that within any single subset of beads, each family of beads thereof has a different fluorescent intensity; and each family of beads is specific for the detection of a strain of HPV different from any other bead family in the beadset; wherein said beadset is capable of identifying one or more specific strains of HPV through analysis of bead size, fluorescent intensity, or sequence discrimination of the at least one bead family or bead subset, using flow cytometry.

The invention is also directed to part to methods for preparing a beadset for differentiating between two or more strains of HPV, the method comprising selecting a plurality of families or subsets of beads based on size, fluorescent intensity, or both, comprising providing:

(a) at least two subsets of beads, wherein each subset of beads is physiochemically distinguishable from any other bead subset based on at least size; or (b) at least one subset of beads having at least two families, wherein the beads in a bead subset are homogeneous in size with respect to each other, and are physiochemically distinguishable into two or more families of beads based on the level of labelling each contains, or (c) a combination of said families of beads and said subsets of beads; and wherein:

the beads within each bead family of a subset are each coupled to an optionally-labelled nucleic acid capture probe capable of binding to a HPV strain-specific region of an HPV genome or, optionally, to at least one of a control nucleic acid sequence, provided that any nucleic acid capture probe or control nucleic acid sequence is labelled with the same label as other labelled capture probes or control nucleic acid sequence in the bead subset, and that within any single subset of beads, each family of beads thereof has a different fluorescent intensity; and each family of beads is specific for the detection of a strain of HPV different from any other bead family in the beadset; wherein said beadset is capable of identifying one or more specific strains of HPV through analysis of bead size, fluorescent intensity, or sequence discrimination of the at least one bead family or bead subset, using flow cytometry.

The methods of the present invention in relation to HPV detection may be used to distinguish to between from 2 and 16 strains of HPV including between 2, 3, 4, 5, 6, 7, 8, 9, 10, 11, 12, 13, 14, 15 and 16 strains. In view of the usefulness of a control, the present invention therefore can use from 2-17 different beads or beadsets. In another embodiment, the beadset comprises at least 16 subsets of beads for HPV strains 6, 11, 16, 18, 31, 33, 35, 39, 45, 51, 52, 56, 58, 59, 66 and 68, and typically a control beadset. Suitable capture probes are those listed in Table 2.

It may be desirable to test for more than 16 strains of an analyte. Thus, the present invention also includes bead sets with 2-30 different beads or bead sets, including 2, 3, 4, 5, 6, 7, 8, 9, 10, 11, 12, 13, 14, 15, 16, 17, 18, 19, 20, 21, 22, 23, 24, 25, 26, 27, 28, 29, and 30 beads or beadsets.

The present invention is directed in part to certain primer pairs for use in any of the numerous PCR techniques for amplification of nucleic acid sequences, wherein the forward and reverse primers optionally have heels conjugated to the 5' terminus of the primer. In certain embodiments the invention is directed to oligonucleotide amplification primer pairs for targeting oncogenic HPV, the forward primer of the pair, selected from the group consisting of

```
TR TTT GTT ACT GTK GTD GAT ACY A
(SEQ ID NO: 1);

CAR YTR TTT GTT ACT GTK GTD GAT A
(SEQ ID NO: 2);

CAR YTR TTT GTT ACT GTK GTD GA
(SEQ ID NO: 3);

AAY CAR YTR TTT GTT ACT GTK GT
(SEQ ID NO: 4);

TTT GTT ACT GTK GTD GAT ACY AC HCG
(SEQ ID NO: 5);

TTT GTT ACT GTK GTD GAT ACY AC HCG YAG
(SEQ ID NO: 6);

GTK GTD GAT ACY AC HCG YAG TAC
(SEQ ID NO: 7) and

GTD GAT ACY AC HCG YAG TAC HAA
(SEQ ID NO: 8);
``` and the reverse primer of the primer pair is selected from the group consisting of

```
TGA AAA ATA AAY TGY AAA TCA TAT TCY TCM MCA TG
(SEQ ID NO: 9);

CAY ARY TGA AAA ATA AAY TGY AAA TC
(SEQ ID NO: 10);

TR CAY ARY TGA AAA ATA AAY TG
(SEQ ID NO: 11); and

TR CAY ARY TGA AAA ATA AA
(SEQ ID NO: 12);
``` wherein the forward and reverse primers are each optionally conjugated to a heel at the 5' terminus of the primer.

Determination of whether binding has occurred between an analyte and a reactant present on a bead may be done using any methodology which allows the differentiation between different beads within the headset. In certain particularly preferred embodiments, the methods of differentiating between different beads within the beadsets utilize flow cytometry.

The present invention further contemplates diagnostic kits for use in accordance with the reagents and methods of the present invention. In particular, the present invention extends to biochips and the miniaturization of the solid phase components of the assay to generate nanoassay reagents. In one embodiment, the bead set or part thereof or other reagents are immobilized to a solid phase such as a biochip. The biochip may also be regarded as a "biolab" on which at least part of the assay is performed and/or results recorded.

A list of abbreviations used herein is provided in Table 1.

TABLE 1

| Abbreviation | Description |
| --- | --- |
| FITC | Fluorescein isothiocyanate |
| HEX | Hexachlorofluorescein |
| HIV | Human Immunodeficiency Virus |
| HPV | Human Papilloma Virus |
| JOE | 7'-dimethoxyfluorescein |
| PCR | Polymerase chain reaction |
| PE | Phycoerythrin |
| PMT | Photomultiplier tube |
| QD | Quantum dot |
| TAMRA | Carboxytetrametylrhodamine |
| TET | Teterachlorofluoresceine |
| TMR | Tetramethylrhodamine |
| VRE | Vancomycin resistant enterococci |

A summary of the sequences used herein are shown in Table 2.

TABLE 2

Sequences (5' being on the left, 3' on the right)

| | Sequence | SEQ ID NO: |
| --- | --- | --- |
| PCR primer sequences | | |
| GP5+ | TTTGTTACTGTGGTAGATACTAC | 13 |
| GP6+ | GAA AAA TAA ACT GTA AAT CAT ATT C | 14 |
| GP5d+ | TTTKTTACHGTKGTDGATACYAC | 15 |
| GP6d+ | GAAAHATAAAYTGYAADTCATAYTC | 16 |
| GP5+ (5Phos) | /5Phos/TTTGTTACTGTGGTAGATACTAC | 17 |
| GP6+ (5AmMC6) | /5AmMC6/GAA AAA TAA ACT GTA AAT CAT ATT C | 18 |
| GP5d+ (5Phos) | /5Phos/TTTKTTACHGTKGTDGATACYAC | 19 |
| GP6d+ (5AmMC6) | /5AmMC6/GAAAHATAAAYTGYAADTCATAYTC | 20 |
| GP5d2+ | TTT KTT ACH GTK GTD GAT ACH AC-3' | 21 |
| T7aGP6d+ (HeelGP6d+) | AAT CTA ATA CGA CTC ACT AT AGG GGA AAH ATA AAY TGY AAD TCA TAY TC | 22 |
| GP5d3+ | TTT GTT ACH GTD GTD GAY ACH AC | 23 |
| T7aGP6d+* (HeelGP6d+) | AAT CTA ATA CGA CTC ACT AT AGG GGA AAH ATA AAY TGY ARD TCA WAY TC | 24 |

TABLE 2-continued

Sequences (5' being on the left, 3' on the right)

| Sequence | | SEQ ID NO: |
|---|---|---|
| GP5d2+ (5Phos) | /5Phos/TTT KTT ACH GTK GTD GAT ACH AC-3' | 25 |
| T7aGP6d+ (HeelGP6d+) (5AmMC6) | /5AmMC6/AAT TCT AAT ACG ACT CAC TAT AGG GGA AAH ATA AAY TGY AAD TCA TAY TC | 26 |
| GP5d3+ (5Phos) | 5Phos TTT GTT ACH GTD GTD GAY ACH AC | 27 |
| T7aGP6d+* (5AmMC6) | /5AmMC6/AAT TCT AAT ACG ACT CAC TAT AGG GGA AAH ATA AAY TGY ARD TCA WAY TC | 28 |
| mlc1_95f | GGC ACC CAG ACA ATA CAC | 29 |
| T7amlc1_275r (HeelMLCR) | AAT TCT AAT ACG ACT CAC TAT AGG GTA AGT TGA AGA GGT GAA GAA | 30 |
| mlc1_95f (5Phos) | /5Phos/GGC ACC CAG ACA ATA CAC | 31 |
| T7amlc1_275r (HeelMLCR) (5AmMC6) | /5AmMC6/AAT TCT AAT ACG ACT CAC TAT AGG GTA AGT TGA AGA GGT GAA GAA | 32 |
| GBHPVf1 | /5Phos/caatcagc TR TTT GTT ACT GTK GTD GAT ACY A | 33 |
| GBHPVf2 | /5Phos/acaat CAR YTR TTT GTT ACT GTK GTD GAT A | 34 |
| GBHPVf3 | /5Phos/acaat CAR YTR TTT GTT ACT GTK GTD GA | 35 |
| GBHPVf3+ | /5Phos/ggaacaat CAR YTR TTT GTT ACT GTK GTD GA | 36 |
| GBHPVf4 | /5Phos/ggaac AAY CAR YTR TTT GTT ACT GTK GT | 37 |
| GBHPVf5 | /5Phos/cagctt TTT GTT ACT GTK GTD GAT ACY AC HCG | 38 |
| GBHPVf6 | /5Phos/cagctt TTT GTT ACT GTK GTD GAT ACY AC HCG YAG | 39 |
| GBHPVf7 | /5Phos/attacc GTK GTD GAT ACY AC HCG YAG TAC | 40 |
| GBHPVf8 | /5Phos/ctgtt GTD GAT ACY AC HCG YAG TAC HAA | 41 |
| GBHPVr1 | /5AmMC6/actcactatagg TGA AAA ATA AAY TGY AAA TCA TAT TCY TCM MCA TG | 42 |
| GBHPVr2 | /5AmMC6/aatacgactcactatagg CAY ARY TGA AAA ATA AAY TGY AAA TC | 43 |
| GBHPVr3 | /5AmMC6/tctaatacgactcactatagg TR CAY ARY TGA AAA ATA AAY TG | 44 |
| GBHPVr4 | /5AmMC6/aattctaatacgactcactatagg TR CAY ARY TGA AAA ATA AA | 45 |
| Capture probe sequences | | |
| Probe 6: | /5Acryd/AAT/iAmMC6T/AA AGG GAG GAC AGC TAT GGA CAT CCG TAA CTA CAT CTT CCA CAT ACA CCA A | 46 |
| Probe 11: | /5Acryd/AAT/iAmMC6T/AA AGG GAG GAC AGC TAT GGA CAT CTG TGT CTA AAT CTG CTA CAT ACA CTA A | 47 |
| Probe 16: | /5Acryd/AAT/iAmMC6T/AA AGG GAG GAC AGC TAT GGA CGT CAT TAT GTG CTG CCA TAT CTA CTT CAG A | 48 |
| Probe 18b: | /5Acryd/AAT/iAmMC6T/AA AGG GAG GAC AGC TAT GGA CC TCC TGT ACC TGG GCA ATA TGA TGC TAC CA | 49 |
| Probe 31: | /5Acryd/AAT/iAmMC6T/AA AGG GAG GAC AGC TAT GGA CTG TTT GTG CTG CAA TTG CAA ACA GTG ATA C | 50 |
| Probe 33: | /5Acryd/AAT/iAmMC6T/AA AGG GAG GAC AGC TAT GGA CTT TAT GCA CAC AAG TAA CTA GTG ACA GTA C | 51 |
| Probe 35: | /5Acryd/AAT/iAmMC6T/AA AGG GAG GAC AGC TAT GGA CGT CTG TGT GTT CTG CTG TGT CTT CTA GTG A | 52 |
| Probe 39: | /5Acryd/AAT/iAmMC6T/AA AGG GAG GAC AGC TAT GGA CTC TAC CTC TAT AGA GTC TTC CAT ACC TTC T | 53 |
| Probe 45: | /5Acryd/AAT/iAmMC6T/AA AGG GAG GAC AGC TAT GGA CAC ACA AAA TCC TGT GCC AAG TAC ATA TGA C | 54 |
| Probe 51: | /5Acryd/AAT/iAmMC6T/AA AGG GAG GAC AGC TAT GGA CAG CAC TGC CAC TGC TGC GGT TTC CCC AAC A | 55 |
| Probe 52: | /5Acryd/AAT/iAmMC6T/AA AGG GAG GAC AGC TAT GGA CTG CTG AGG TTA AAA AGG AAA GCA CAT ATA A | 56 |
| Probe 56: | /5Acryd/AAT/iAmMC6T/AA AGG GAG GAC AGC TAT GGA CGT ACT GCT ACA GAA CAG TTA AGT AAA TAT G | 57 |
| Probe 58b: | /5Acryd/AAT/iAmMC6T/AA AGG GAG GAC AGC TAT GGA CG CAC TGA AGT AAC TAA GGA AGG TAC | 58 |
| Probe 59: | /5Acryd/AAT/iAmMC6T/AA AGG GAG GAC AGC TAT GGA CTC TAC TAC TTC TTC TAT TCC TAA TGT ATA C | 59 |
| Probe 66: | /5Acryd/AAT/iAmMC6T/AA AGG GAG GAC AGC TAT GGA CTA TTA ATG CAG CTA AAA GCA CAT TAA CTA A | 60 |
| Probe 68: | /5Acryd/AAT/iAmMC6T/AA AGG GAG GAC AGC TAT GGA CTC TAC TAC TAC TGA ATC AGC TGT ACC AAA T | 61 |
| Probe 68b: | /5Acryd/AAT/iAmMC6T/AA AGG GAG GAC AGC TAT GGA CT CCA CTA CTA CAG ACT CTA CTG TAC CA | 62 |
| Probe MLC_Int: | /5Acryd/AAT/iAmMC6T/AA AGG GAG GAC AGC TAT GGA CCA AAC ACA GAC ACA GAG AGA CCC ACA GAC A | 63 |
| Block Oligo Sequences* | | |
| block6/4: | TTG GTC TAT GTC GAA GAA GTA GTA ACG GAT | 64 |
| block11/4: | TTA GTC TAT GTT GCA GAA TTA GAC ACA GAT | 65 |
| block16/4: | TCT GAT GTA GAA ATG GCT GCA CAA AAT GAC | 66 |
| block18b/4: | TGG TAC CAT CAA ATT GCC CAG GTT CAG GAG | 67 |
| block31/4: | GTA TCT CTG TTA GCA ATA GCA GCT GAA ACA | 68 |
| block33/4: | GTA CTC TCA CTT GTT ACA TGT GTC CAT AAA | 69 |
| block35/4: | TCA CTT GAA GAC ACA GCT GAA CAG ACA GAC | 70 |
| block39/4: | AGA AGC TAT GGT AGA CTC TAT AGT GGT AGA | 71 |
| block45/4: | GTC ATC TGT ACA TGG CAG AGG ATA TTG TGT | 72 |
| block51/4: | TGT TGC GGA AAC CGC AGC AGT GGC AGT GCT | 73 |
| block52/4: | TTA TAT GTG CTT TCC TTT TTA ACC TCA GCA | 74 |

TABLE 2-continued

Sequences (5' being on the left, 3' on the right)

| Sequence | | SEQ ID NO: |
|---|---|---|
| block56/4: | CAT ATA TAC TTT ACT GTA CTG TAC CAG TAC | 75 |
| block58b/4: | TA CCA TCC TTT GTT ACA TCA GTC C | 76 |
| block59/4: | GTA TAG ATT AGC AAT AGT AGA AGA AGT AGA | 77 |
| block66/4: | TTA GTA AAT GTC CTT TTT GCT GCT TTA ATA | 78 |
| block68/4: | ATT TGC TAC AGG TGA TTG AGT AGA AGT AGA | 79 |
| block68b/4: | TGG TAG AGT AGT GTC TGA AGT AGA GGA | 80 |
| blockMLC/4: | TGT CTC TGG GTG TCT CTC TGT CTC TGT TTG | 81 |

Signal Oligos Sequences

| HPV signal a: | /5AmMC6/TTT TTT CAT GKK GAR GAR TAT GA/3Phos/ | 82 |
| HPV signal b: | /5AmMC6/TTT TTT CAT GKK GAR GAR TAT/3Phos/ | 83 |
| MLC signal a: | /5AmMC6/TTT TTT ACA GAC ACA GAC AAC/3Phos/ | 84 |
| MLC signal b: | /5AmMC6/TTT TTT ACA GAC ACA GAC AAC A/3Phos/ | 85 |
| MLC signal c: | /5AmMC6/TTT TTT ACA GAC ACA GAC AAC AC/3Phos/ | 86 |

*Wherein the shaded bases correspond to the differences.
The following variables are used herein:
"K" is a variable for G or T;
"H" is a variable for the nucleotides T, A, or C;
"M" is a variable for the nucleotides A or C;
"Y" is a variable for the nucleotides T or C;
"R" is a variable for the nucleotides A or G;
"W" is a variable for the nucleotides A or T;
"D" is a variable for the nucleotides A, T, or G;
3Phos is a 3' phosphate group;
5Phos is a 5' phosphate group; and,
5AmMC6 is a 5' $H_2N$—$(CH_2)_6$— group attached via a phosphate group.

BRIEF DESCRIPTION OF THE FIGURES

FIG. 5 is a schematic diagram showing an example of the binding agents that can be used in the array. The array comprises microspheres comprising diameters of 3.0 μm, 3.5 μm, 4.1 μm, 5.0 μm, 5.6 μm and 6.8 μm and fluorescent label signal intensities of 0%, 4%, 20% and 100%. In the case of the smaller bead sizes, i.e., 3.0 μm, 3.5 μm, and 4.1 μm, TMR intensities of 0% and 100% were used; for the 5.0 μm microspheres TMR intensities of 0%, 20% and 100% were used; and for the largest microspheres, the 5.6 μm and 6.8 μm diameter, all signal intensities were used.

FIG. 6 shows an example of a beadset of the present invention.

DETAILED DESCRIPTION OF THE INVENTION

Figure 1:
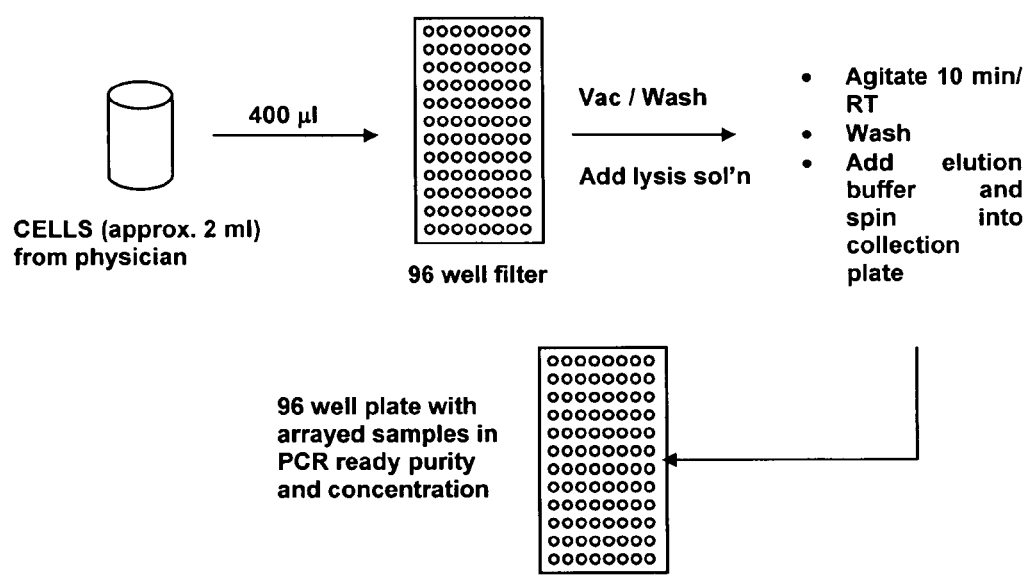
FIG. 1 is a graphical representation showing a schematic of an example of a DNA extraction protocol used in the HPV diagnostic method.

The present invention provides assays and reagents including biochips which enable the detection of one or more analytes and/or to differentiate between members within a class of analytes. In particular, analytes are identified or distinguished by methods of multiplexing analysis based on the properties of the analytes and of the assay components. The diagnostic and detection assays and reagents of the present invention have particular application in the diagnosis of pathogen infections in multicellular eukaryotic subjects. In one particular embodiment, the present invention provides a diagnostic assay for HPV in human subjects and is able to differentiate between HPV taxons in order to distinguish "high risk" HPV infections from "low risk" HPV infections. Furthermore, the present invention also provides methods of diagnosing or assessing the risk of development of a disease associated with an infection by an analyte in a multicellular eukaryotic subject including, inter alia, cervical cancer in a human subject.

It is to be understood that unless otherwise indicated, the subject invention is not limited to specific diagnostic or assay protocols, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context already dictates otherwise. Thus, for example, reference to "an analyte" includes a single analyte as well as two or more analytes; a "physiochemically distinguishable substrate" includes a single substrate as well as two or more substrates; reference to "a target" includes a single target, as well as two or more targets; reference to "an amplification" includes a single amplification, as well as multiple amplification steps; reference to "the amplicon" includes a single or multiple or complex amplicons; and so forth.

Accordingly, in one aspect, the present invention provides beadsets which are capable of detecting, and/or differentiat ing between two or more analytes in a sample, said beadsets comprising:

(a) the beads of each subset are homogeneous with respect to size;

(b) the beads within each subset are coupled to a reactant that will specifically react with a given analyte of interest in a sample to be tested;

(c) the reactant on each bead is labelled with the same label with each subset of beads having a different fluorescent intensity to create a heterogeneous mixture of subsets of beads based on fluorescent intensity; and (d) at least two subsets of beads are mixed together to produce a beadset, wherein the subset identity and therefore the reactant to which the bead has been coupled is identifiable by flow cytometry based on size, fluorescent intensity and analyte discrimination.

In some embodiments, the reactants may be further differentially labelled to create additional subpopulations of beads based on the incorporation of different fluorochromes.

In other embodiments, the present invention provides methods or beadsets for the detection and/or differentiation of an analyte.

In certain preferred aspects, the methods or beadsets of the present invention are able to detect and/or differentiate pathogenic analytes.

The present invention also provides methods for detecting and/or differentiating between one or more analytes in a sample comprising the steps of:

(a) contacting the sample with a beadset specific for the analytes of interest;

(b) incubating said beadset with said sample for a time and under conditions sufficient to allow said analyte(s) in said sample to react specifically with a reactant on a bead within said beadset; and (c) detecting and/or differentiating analytes in the sample which are bound to a reactant on said bead.

As used herein, the term "pathogenic analyte" refers to a microorganism or virus which putatively infects, colonizes or has otherwise contaminated the sample. Exemplary pathogen analytes include viruses, bacteria, fungi and eukaryotic microorganisms. In a preferred embodiment, "analyte" includes a microorganism or virus which infects a multicellular organism such as an animal or plant. Accordingly, in some embodiments the pathogenic analytes may be regarded as an animal or plant pathogen. However, the present invention encompasses the detection and differentiation of non-pathogenic analyte which colonize multicellular organisms such as microbial symbionts of animals (e.g., *Lactobacillus* spp., ruminant bacteria), microbial symbionts of insects (e.g., *Streptomyces* spp., *Wolbachia* spp.), microbial symbionts of sponges (e.g., green algae, dinoflagellates, cyanobacteria) and the like; endophytes of plants (e.g., Mycorrhiza, *Rhizobium* spp., *Frankia* spp., *Streptomyces* spp.); and the like. Furthermore, the analyte may be an analyte which is not associated with a multicellular organism. Such analytes include bacteria, fungi, viruses, protists, nematodes and the like which colonize particular environments including "natural" environments such as soil, oceans, fresh water, ice, rock, hydrothermal vents and air; health care environments including hospitals, hospital equipment, surgical equipment, health care staff garments and the like; "industrial" environments including manufacturing facilities, pharmaceutical facilities, breweries, wineries and the like; "laboratory" environments including fermenters, cultures, benches, equipment and the like.

Accordingly, samples contemplated by the present invention include industrial samples such as air, water, and soil, and the like, and biological samples such as blood, serum, saliva, faeces, urine, tissue fluid, semen, exudate, pus, respiratory fluid and mucus and swabs from topical sores, cancers and lesions. In addition, a sample may be an extraterrestrial sample such as from a meteorite or on another planet. In regards to the latter, the assay of the present invention may be adapted for use on an interplanetary remote vehicle for testing of soil or dust or ice samples or for testing core material in a planet.

In some preferred embodiments, the analyte comprises a bacterium, fungus, virus and/or eukaryotic parasite which infects an animal subject. "Animal subjects" contemplated herein include any animal, preferably a mammal and more preferably a primate including a lower primate and even more preferably, a human. For convenience, an "animal" also specifically includes livestock species such as cattle, horses, sheep, pigs, goats and donkeys as well as laboratory animals including mice, rats, rabbits, guinea pigs and hamsters.

Exemplary human analytes which may be detected using the reagents and methods of the present invention include viruses such Human papilloma virus (HPV), coronaviruses including the SARS virus, influenza viruses, avian flue virus, HIV including HIV-1, HIV-II or HLTV-IV, Lentiviruses in general, hepatitis viruses and the like, the pathogenic agents of sexually transmitted diseases such as *Chlamydia, Gonorrhoea, Mycoplasma* spp. and Syphilis; Food-borne pathogens such as *Listeria* spp., *Salmonella* spp., *E. coli* (particularly *E. coli* HO 567), *Shigella* spp., *Brucella* spp., *Staphylococcus aureus*; Nosicomial pathogens such as *S. aureus* including Methicillin-Resistant *S. Aureus* (MRSA) and enterococci including Vancomycin Resistant Enterococci (VRE); Environmentally acquired pathogens such as *Legionella* spp., *Giardia* spp., *Crytospiridium* spp., *Bacillus* anthacis (anthrax) and the like.

In other aspects, the sample in which the analyte is detected is preferably a sample derived from a multicellular subject which is putatively infected or colonized by the analyte. Therefore, in one aspect, the sample is preferably a "biological sample". Exemplary biological samples which in no way limit the present invention include tissue or cell samples such as cell scapes, biopsies and the like and body fluid samples including blood, urine, lymph, amniotic fluid, cerebrospinal fluid and the like.

In certain other aspects, the methods of the present invention are also applicable to the detection of an "analyte" in a sample which is not exclusively derived from a multicellular eukaryotic organism. As such, the present invention extends to detecting, and/or differentiating between, one or more particular taxons or strains of analytes in samples such as environmental samples (including air, water and soil samples), industrial samples, laboratory samples and the like. For example, the methods of the present invention may be used to assess the prokaryotic microflora, eukaryotic microflora and or viral load of a soil, water or air sample or a sample derived from a man-made object or surface.

In some particularly preferred embodiments of the present invention, the analyte to be detected is HPV or a strain thereof and the sample is preferably a biological sample derived from a human subject. In a further preferred embodiment, the biological sample comprises one or more cells of the subject, blood or urine. Most preferably, the biological sample comprises cervical cells collected from the subject. HPV is described in detail by Gearhart et al. which is reproduced in part below. HPVs produce epithelial tumors of the skin and mucous membranes. Over 100 HPV types have been detected, and the genomes of almost 70 have been sequenced completely. The current classification system, which is based on similarities in their genomic sequences, generally correlates with the 3 categories used to describe HPV clinically: anogenital and/or mucosal, nongenital cutaneous, and epidermodysplasia verruciformis (EV). A database of HPV genomic sequences and a phylogenic tree are available via the Internet at HPV Sequence Database.

The mucosal HPV infections are classified further as latent (asymptomatic), subclinical, or clinical. Clinical lesions are grossly apparent, whereas latent infections are detected only by tests for viral DNA. Subclinical lesions are identified by application of 5% acetic acid and inspection under magnification. Most HPV infections are latent; clinically apparent infections usually result in warts rather than malignancies.

HPV types 6 and 11 are typically labelled as low risk because infection with these types has low oncogenic potential and usually results in the formation of condylomata and low-grade precancerous lesions. HPV types 16 and 18 have emerged as the high-risk types of HPV because they are responsible for most high-grade intraepithelial lesions that may progress to carcinomas, particularly those in the anogenital and/or mucosal category.

HPV infection alone does not cause malignant transformation of infected tissue. Cofactors, such as tobacco use, ultraviolet radiation, pregnancy, folate deficiency, and immune suppression have been implicated in this process. Table 3 lists a variety of diseases and the associated HPV subtypes.

TABLE 3

Diseases and Associated HPV Subtypes

| | HPV Type |
|---|---|
| Nongenital Cutaneous Disease | |
| Common warts (verrucae vulgaris) | 1, 2, 4, 26, 27, 29, 41, 57, 65 |
| Plantar warts (myrmecias) | 1, 2, 4, 63 |
| Flat warts (verrucae plana) | 3, 10, 27, 28, 38, 41, 49 |
| Butcher's warts (common warts of people who handle meat, poultry, and fish) | 1, 2, 3, 4, 7, 10, 28 |
| Mosaic warts | 2, 27, 57 |
| Ungual squamous cell carcinoma | 16 |
| Epidermodysplasia verruciformis (benign) | 2, 3, 10, 12, 15, 19, 36, 46, 47, 50 |
| Epidermodysplasia verruciformis (malignant or benign) | 5, 8, 9, 10, 14, 17, 20, 21, 22, 23, 24, 25, 37, 38 |
| Nonwarty skin lesions | 37, 38 |
| Nongenital Mucosal Disease | |
| Respiratory papillomatosis | 6, 11 |
| Squamous cell carcinoma of the lung | 6, 11, 16, 18 |
| Laryngeal papilloma | 6, 11, 30 |
| Laryngeal carcinoma | 16, 18 |
| Maxillary sinus papilloma | 57 |
| Squamous cell carcinoma of the sinuses | 16, 18 |
| Conjunctival papillomas | 6, 11 |
| Conjunctival carcinoma | 16 |
| Oral focal epithelial hyperplasia (Heck disease) | 13, 32 |
| Oral carcinoma | 16, 18 |
| Oral leukoplakia | 16, 18 |
| Squamous cell carcinoma of the esophagus | 16, 18 |
| Anogenital Disease | |
| Condylomata acuminata | 6, 11, 30, 42, 43, 44, 45, 51, 52, 54 |
| Bowenoid papulosis | 16, 18, 34, 39, 42, 45 |
| Bowen disease | 16, 18, 31, 34 |
| Giant condylomata (Buschke-Löwenstein tumors) | 6, 11 |
| Unspecified intraepithelial neoplasia | 30, 34, 39, 40, 53, 57, 59, 61, 62, 64, 66, 67, 68, 69 |
| Low-grade intraepithelial neoplasia | 6, 11, 43 |
| Intermediate intraepithelial neoplasia | 31, 33, 35, 42, 44, 45, 51, 52 |

TABLE 3-continued

Diseases and Associated HPV Subtypes

| | HPV Type |
|---|---|
| High-grade intraepithelial neoplasia | 16, 18, 56, 58 |
| Carcinoma of vulva | 6, 11, 16, 18 |
| Carcinoma of vagina | 16 |
| Carcinoma of cervix | 16, 18, 31 |
| Carcinoma of anus | 16, 31, 32, 33 |
| Carcinoma in situ of penis (erythroplasia of Queyrat) | 16 |
| Carcinoma of penis | 16, 18 |

Papillomaviruses are highly species specific and do not infect other species, even under laboratory conditions. Humans are the only known reservoir for HPV.

Papillomaviruses are nonenveloped viruses of icosahedral symmetry with 72 capsomeres that surround a genome containing double-stranded circular DNA with approximately 8000 base pairs.

Papillomaviruses are thought to have two modes of replication, i.e., stable replication of the episomal genome in basal cells and runaway, or vegetative, replication in more differentiated cells to generate progeny virus. Although all cells of a lesion contain the viral genome, the expression of viral genes is tightly linked to the state of cellular differentiation. Most viral genes are not activated until the infected keratinocyte leaves the basal layer. Production of virus particles can occur only in highly differentiated keratinocytes; therefore, virus production only occurs at the epithelial surface where the cells are ultimately sloughed into the environment.

HPV lesions are thought to arise from the proliferation of infected basal keratinocytes. Infection typically occurs when basal cells are exposed to infectious virus through a disturbed epithelial barrier as would occur during sexual intercourse or after minor skin abrasions. HPV infections have not been shown to be cytolytic, rather viral particles are released as a result of degeneration of desquamating cells. Furthermore, the HPV virus can survive for many months and at low temperatures without a host.

Virus multiplication is generally confined to the nucleus. Consequently, infected cells usually exhibit a high degree of nuclear atypia. Koilocytosis (from the Greek koilos, meaning empty) describes a combination of perinuclear clearing (halo) with a pyknotic or shrunken (rasinoid) nucleus and is a characteristic feature of productive papillomavirus infection.

The HPV genome exists as a circular episomal DNA separate from the host cell nucleus in benign or low-risk HPV lesions, such as those typically associated with HPV types 6 and 11. The genomes of high-risk HPV types 16 and 18 are typically integrated into the host cell DNA in malignant lesions. The present invention, however, extends to any strain of HPV including but not limited to strains 6, 11, 16, 18, 31, 33, 35, 39, 45, 51, 52, 56, 58, 59, 66 and 68. Integration of the viral genome into the host cell genome is considered a hallmark of malignant transformation. HPV proteins E6 and E7 of high-risk serotypes have been shown to inactivate the host's tumor suppressor proteins p53 and Rb, thereby resulting in unregulated host cell proliferation and malignant transformation.

Therefore, in other aspects, the present invention provides methods for detecting, and/or differentiating between, one or more particular strains of HPV in a biological sample, said methods comprising the steps of:

(i) obtaining a biological sample which putatively comprises HPV from a human subject;
(ii) isolating nucleic acid from said sample;

(iii) amplifying the nucleic acid from said sample using primers which generate an amplicon which is distinct for each strain of HPV;
(iv) optionally amplifying a control nucleic acid sequence;
(v) effecting labelling of the amplicon(s) recited at steps (iii) and/or (iv);
(vi) hybridizing the labelled amplicon(s) to a beadset coated with reactants wherein each member of the beadset comprises a nucleic acid molecule having complementarity to a nucleotide sequence of a particular strain of HPV or a control nucleotide sequence, bound or otherwise associated with a physiochemically distinguishable bead; and
(vii) determining to which of the reactants an amplicon has bound;
wherein the association of an amplicon with a particular reactant is indicative of the presence of a particular strain of HPV in the sample.

In yet other aspects, the hybridizing occurs in the presence of at least one signal oligonucleotide sequence.

In still other aspects, the hybridizing occurs in the presence of at least one blocking oligonucleotide sequence.

The present invention enables the detection of amplified HPV DNA or, with the use of a reverse transcriptase, corresponding RNA. Hence, the present invention contemplates beads with RNA or DNA or chemical analogs thereof.

The methods of the present invention are predicated, in part, on detecting and/or differentiating between one or more particular strains of a subject analyte in a sample. Reference herein to "particular strains of a subject analyte" includes any variants of the species or taxon of the analyte. Examples of "strains" of an analyte include sub-species of the analyte, variants of the analyte with differing levels of virulence, variants of the analyte which indicate different prognoses when infecting or colonizing a host, biochemical variants of the analyte and the like.

In some preferred embodiments, the methods of the present invention may be adapted to detecting and/or differentiating between particular strains of HPV which are associated with higher risk or higher oncogenic potential in humans (high risk strains) and those which are associated with lower carcinoma risk or low oncogenic potential (low risk strains). Accordingly, the term "high risk" strain of HPV includes any strain of HPV which is associated with the development of carcinoma, including cervical cancer, in human subjects. As indicated above, exemplary high risk strains of HPV, which in no way limits the invention, include HPV 16, 18, 31, 33, 35, 39, 45, 51, 52, 56, 58, 59, 66 and 68. Suitable capture probes on the beads for these strains of HPV are shown in Table 2. The term "probe" and "primer" may be used interchangeably in this context. "Low risk" strains of HPV include those which are not associated or only weakly associated with increased risk of carcinoma in human subjects. Typically, the low-risk strains of HPV are the wart-forming strains, including HPV 6 and HPV 11.

The beads of the present invention are coupled to reactants which will specifically interact with a given analyte of interest within a sample. In some aspects, the reactants of the present invention are nucleic acids and the analytes within the sample which specifically react with the reactant are also nucleic acids.

Hence, this aspect of the subject invention uses primers which are directed to conserved regions of a strain of HPV but which flank strain-specific genomic sequences. The strain-specific sequences are referred to as "variable" sequences since they vary between strains compared to the conserved sequences which are constant between strains. Upon amplification, the amplicons are put into contact with subsets of beads in the beadset wherein each bead of each subset carries a capture nucleic acid primer or probe capable of hybridizing to the strain-specific amplicons. Multiplexing using bead size, fluorescence intensity and DNA binding specificity enables identification, sorting and distinguishing of HPV strains.

Accordingly, other aspects of the present invention contemplates beadsets for detecting one or more strains of HPV and/or for differentiating between two or more strains of HPV, wherein the beadset comprises a plurality of families or subsets of beads wherein:
(a) the beads of each subset are homogeneous with respect to size;
(b) the beads within each subset are coupled to a nucleic acid capture probe which is capable of binding to a HPV strain-specific region of an HPV genome or, optionally, a control nucleic acid sequence;
(c) the capture probe on each bead is labelled with the same label with each subset of beads having a different fluorescent intensity to create a heterogeneous mixture of beads based on fluorescent intensity; and
(d) at least two subsets of beads are mixed together to produce a beadset, wherein the subset identity and therefore the strain of HPV is identifiable by flow cytometry based on size, fluorescent intensity and sequence discrimination.

Still other aspects of the present invention contemplate a methods for detecting and/or differentiating between two or more HPV strains in a sample, comprising the steps of:
(a) contacting the sample with a beadset comprising a plurality of families or subsets of beads wherein:
  (i) the beads of each subset are homogeneous with respect to size;
  (ii) the beads within each subset are coupled to a nucleic acid capture probe which is capable of binding to a HPV strain-specific region of an HPV genome or, optionally, a control nucleic acid sequence;
  (iii) the capture probe on each bead is labelled with the same label with each subset of beads having a different fluorescent intensity to create a heterogeneous mixture of beads based on fluorescent intensity; and
  (iv) at least two subsets of beads are mixed together to produce a beadset, wherein the subset identity and therefore the strain of HPV is identifiable by flow cytometry based on size, fluorescent intensity and sequence discrimination;
(b) incubating said beadset with said sample for a time and under conditions sufficient to allow said primers to bind to the HPV genome amplified to generate a replicon comprising a strain-specific region;
(c) detecting and/or differentiating the amplicons generated in the sample which are bound to said beads to thereby identify or distinguish between the two or more HPV strains.

The amplicons to which the nucleic acid capture probes are specific may also be labelled with a fluorescent reporter molecule.

Nucleic acids may be isolated from the subject sample using any method which is convenient with regard to the nature of the sample itself and the analyte. As used herein, the term "nucleic acid" refers to DNA and/or RNA. Typically, DNA is isolated, although under some circumstances which would be evident to one of skill in the art, it may be more preferable to isolate RNA, for example, when the analyte of interest is an RNA virus. If RNA is isolated, the RNA may be amplified, or the RNA may be reverse transcribed into cDNA using standard methods, for subsequent amplification and analysis.

Preferably, the "nucleic acid" is DNA. DNA may be isolated from the sample using any convenient means. For example, in the case of a virus such as HPV in a human cell sample, guanidine or a functionally equivalent agent may be used to lyse the cells. An exemplary guanidine-based method for cell lysis and DNA extraction is the method of Nelson and Krawetz (*Anal. Biochem.* 207(1):97-201, 1992). Guanidine-based lysis solutions are also commercially available from suppliers such as Qiagen, e.g., QIAamp, PAXgene, and the like. However, methods of lysis may change depending on the nature of the sample and analyte. For example, for the detection of an analyte in an environmental sample such as a soil or sediment sample, a glass-bead based cell lysis system may be more appropriate, such as the method of Kuske et al. (*Appl. Environ. Microbiol.* 64(7):2463-2472, 1998). In any event, the appropriate lysis protocol for a given analyte and sample would be readily determined by one of ordinary skill in the art with no undue experimentation.

After lysis of the cells, the DNA may be purified by any convenient means which would be readily evident to one of skill in the art (e.g., see commercially available kits hereinabove). In certain preferred embodiments of the invention, the DNA is purified using a limiting amount of a DNA binding agent such as, but not limited to, silica. By using a limiting amount of the DNA binding agent, a uniform amount of DNA may be isolated from different samples as the amount of DNA recovered in each case is equal to the maximum amount of DNA that can be bound by the limiting amount of DNA binding agent. The DNA bound to the DNA binding agent may then be recovered or eluted from the DNA binding agent using any convenient means.

Although DNA is a preferred nucleic acid, RNA may also be isolated from the sample using any standard RNA isolation'protocol. RNA isolation typically involves a cell disruption step and an RNA isolation step. Exemplary cell disruption techniques which are suitable for the isolation of RNA include those presented in Ambion Technical Bulletin #183. Furthermore, a range of exemplary RNA isolation kits which are suitable for a range of sample types. However, it should be understood that the present invention is not in any way limited by these specific methods and kits for RNA isolation and purification and the present invention is compatible with any RNA isolation methods which would be evident to one of skill in the art.

The beadset may comprise, in relation to HPV detection as many subsets of beads as strains of HPV. Hence, the assay may employ 2, 3, 4, 5, 6, 7, 8, 9, 10, 11, 12, 13, 14, 15 or 16 subsets of beads each for HPV strains 6, 11, 16, 18, 31, 33, 35, 39, 45, 51, 52, 56, 58, 59, 66 and 68. Additional beads may also be used for controls. Suitable capture probes are disclosed in Table 2.

Hence, other aspects of the present invention are directed to beadsets for detecting one or more strains of HPV and/or for differentiating between two or more strains of HPV, wherein the beadset comprises a plurality of families or subsets of beads wherein:

(a) the beads of each subset are homogeneous with respect to size;

(b) the beads within each subset are coupled to a nucleic acid capture probe selected from the list in Table 2 that is capable of binding to a HPV strain-specific region of an HPV genome or, optionally, a control nucleic acid sequence;

(c) the capture probe on each bead is labelled with the same label with each subset of beads having a different fluorescent intensity to create a heterogeneous mixture of beads based on fluorescent intensity; and (d) at least two subsets of beads are mixed together to produce a beadset, wherein the subset identity and therefore the strain of HPV is identifiable by flow cytometry based on size, fluorescent intensity and sequence discrimination.

Still a further aspect of the present invention contemplates methods for detecting and/or differentiating between two or more HPV strains in a sample, comprising the steps of:

(a) contacting the sample with a beadset comprising a plurality of families or subsets of beads wherein:

(i) the beads of each subset are homogeneous with respect to size;

(ii) the beads within each subset are coupled to a nucleic acid capture probe is selected from the list in Table 2 that is capable of binding to a HPV strain-specific region of an HPV genome or, optionally, a control nucleic acid sequence;

(iii) the capture probe on each bead is labelled with the same label with each subset of beads having a different fluorescent intensity to create a heterogeneous mixture of beads based on fluorescent intensity; and (iv) at least two subsets of beads are mixed together to produce a beadset, wherein the subset identity and therefore the strain of HPV is identifiable by flow cytometry based on size, fluorescent intensity and sequence discrimination;

(b) incubating said beadset with said sample for a time and under conditions sufficient to allow said probes to bind to the HPV genome amplified to generate a replicon comprising a strain-specific region; and (c) detecting and/or differentiating the amplicons generated in the sample which are bound to said beads to thereby identify or distinguish between the two or more HPV strains.

Accordingly, the beadsets may comprise 2, 3, 4, 5, 6, 7, 8, 10, 11, 12, 13, 14, 15, 16 subsets of beads each with one of a nucleic acid molecule selected from the listing in Table 2. Reference to these HPV strain-specific sequences in Table 2 includes nucleic acid molecules having at least 90% identity to these sequences or capable of hybridizing thereto or their complementary forms under low stringency conditions. Reference to at least 90% includes 90, 91, 92, 93, 94, 95, 96, 97, 98, 99 and 100%.

The methods of the present invention rely, in part, on amplifying a nucleic acid from a sample using primers that bind to conserved sequences among different strains of the subject analyte, but which generate an amplicon which comprises a distinct nucleotide sequence for each strain of the analyte. In effect, the primers used in the present invention bind to sequences which are conserved among strains of the subject analyte which flank regions that are at least partially non-conserved or polymorphic between strains. Schematically, the amplified region in the analyte has the general structure of:

$$C-X-C'$$

wherein:

C is a nucleotide sequence which is conserved among two or more strains of the analyte and is the binding site of the "forward" primer;

X is a nucleotide sequence, part or all of which comprises variation between different strains of the analyte;

C' is a nucleotide sequence which is conserved among two or more strains of the analyte and is the binding site of the "reverse" primer.

In certain embodiments it is desirable to incorporate heels into one or more of the primers to modify the nucleic acid amplification process. Preferably, these heels are conjugated to the 5' terminus of a primer. More preferably, one or more heels are optionally further conjugated to a 5 Phos or 5AmMC6 moiety at the heel's 5' terminus. In certain preferred embodiments, the heels conjugated to forward primers are selected from: caatcagc, acaat, ggaac, cagctt, attacc, and ctgtt, more preferably acaat and ctgtt. In other preferred embodiments, the heels conjugated to reverse primers are selected from: actcactatagg (SEQ ID NO: aatacgactcactatagg (SEQ ID NO: 88), tctaatacgactcactatagg (SEQ ID NO: 89), and aattctaatacgactcactatagg (SEQ ID NO: 90) more preferably actcactatagg (SEQ ID NO: 87) and tctaatacgactcactatagg (SEQ ID NO: 89).

In certain embodiments related to oligonucleotide amplification primer pairs for targeting oncogenic HPV, the forward primer of a primer pair is selected from the group consisting of:

```
/5Phos/caatcagc TR TTT GTT ACT GTK GTD GAT ACY A
(SEQ ID NO: 33);

/5Phos/acaat CAR YTR TTT GTT ACT GTK GTD GAT A
(SEQ ID NO: 34);

/5Phos/acaat CAR YTR TTT GTT ACT GTK GTD GA
(SEQ ID NO: 35);

/5Phos/ggaac AAY CAR YTR TTT GTT ACT GTK GT
(SEQ ID NO: 37);

/5Phos/cagctt TTT GTT ACT GTK GTD GAT ACY AC HCG
(SEQ ID NO: 38);

/5Phos/cagctt TTT GTT ACT GTK GTD GAT ACY AC HCG
YAG (SEQ ID NO: 39);

/5Phos/attacc GTK GTD GAT ACY AC HCG YAG TAC
(SEQ ID NO: 40); and

/5Phos/ctgtt GTD GAT ACY AC HCG YAG TAC HAA
(SEQ ID NO: 41);
``` and the reverse primer of a primer pair is selected from the group consisting of
/5AmMC6/actcactatagg TGA AAA ATA AAY TGY AAA TCA TAT TCY TCM MCA TG (SEQ ID NO: 42);
/5AmMC6/aatacgactcactatagg CAY ARY TGA AAA ATA AAY TGY AAA TC (SEQ ID NO: 43);
/5AmMC6/tctaatacgactcactatagg TR CAY ARY TGA AAA ATA AAY TG (SEQ ID NO: 44); and
/5AmMC6/aattctaatacgactcactatagg TR CAY ARY TGA AAA ATA AA (SEQ ID NO: 45). As shown, a primer is indicated in capital letters and an optional heel in each instance is shown in underlined lower case letters. Preferably, the forward primer of a primer pair is selected from: /5Phos/acaat CAR YTR TTT GTT ACT GTK GTD GA (SEQ ID NO: 35) and /5Phos/ctgtt GTD GAT ACY AC HCG YAG TAC HAA (SEQ ID NO: 41). In other preferable embodiments, the reverse primer of a primer pair is selected from /5AmMC6/actcactatagg TGA AAA ATA AAY TGY AAA TCA TAT TCY TCM MCA TG (SEQ ID NO: 42) and /5AmMC6/tctaatacgactcactatagg TR CAY ARY TGA AAA ATA AAY TG (SEQ ID NO: 44).

In certain aspects of the invention, the primers incorporate a non-primer binding region 5' extraneous nucleotide sequence conjugated to the 5' end of a 3' template binding primer region. The 5' extraneous nucleotide sequence is conveniently referred to herein as a "heel," "heel clamp," "heel sequence," or "extraneous heel sequence," but this is not in any way intended to be limiting on the subject invention.

In certain preferred embodiments, at least one of the forward and reverse primers is conjugated to a heel at the 5' terminus of the primer. Preferably, when the forward primer is conjugated to a heel at the 5' terminus of the forward primer, the forward primer heel is selected from the group consisting of:

```
CAATCAGC, ACAAT, GGAACAAT, GGAAC, CAGCTT,

ATTACC, CTGTT, /5Phos/CAATCAGC,

/5Phos/ACAAT, /5Phos/GGAACAAT, /5Phos/GGAAC,

/5Phos/CAGCTT, 5Phos/ATTACC,
and

/5Phos/CTGTT.
```

Preferably when the reverse primer is conjugated to a heel at the 5' terminus of the reverse primer, the reverse primer heel is selected from the group consisting of:

```
ACTCACTATAGG (SEQ ID NO: 87),

AATACGACTCACTATAGG
(SEQ ID NO: 88),

TCTAATACGACTCACTATAGG
(SEQ ID NO: 89),

AATTCTAATACGACTCACTATAGG
(SEQ ID NO: 90),

/5AmMC6/ACTCACTATAGG
(SEQ ID NO: 91),

/5AmMC6/AATACGACTCACTATAGG
(SEQ ID NO: 92),

/5AmMC6/TCTAATACGACTCACTATAGG
(SEQ ID NO: 93), and

/5AmMC6/AATTCTAATACGACTCACTATAGG
(SEQ ID NO: 94).
```

In some more preferred embodiments of oligonucleotide amplification primer pairs containing an optional heel nucleic acid sequence, the forward primer of the primer pair is selected from the group consisting of

```
CAR YTR TTT GTT ACT GTK GTD GA,
(SEQ ID NO: 3),
optionally having a ACAAT,
/5Phos/ACAAT, GGAACAAT, or a /5Phos/GGAACAAT
conjugated to the 5' terminus of the primer;
and GTD GAT ACY AC HCG YAG TAC HAA,
(SEQ ID NO: 8)
optionally having a CTGTT or
/5Phos/CTGTT conjugated to the 5' terminus of
the primer.
```

In some more preferred embodiments of oligonucleotide amplification primer pairs containing an optional heel nucleic acid sequence, the reverse primer of the primer pair is selected from the group consisting of:

```
TGA AAA ATA AAY TGY AAA TCA TAT TCY TCM MCA TG,
(SEQ ID NO: 9)
optionally having a ACTCACTATAGG (SEQ ID NO: 87)
or /5AmMC6/ACTCACTATAGG (SEQ ID NO: 91)
conjugated to the 5' terminus of the primer, TR CAY ARY TGA AAA ATA AAY TG,(SEQ ID NO: 11),
optionally having a
```

```
TCTAATACGACTCACTATAGG (SEQ ID NO: 89)
or /5AmMC6/
TCTAATACGACTCACTATAGG (SEQ ID NO: 93)
conjugated to the 5' terminus of the primer;
and TR CAY ARY TGA AAA ATA A, (SEQ ID NO: 12),
optionally having a
TCTAATACGACTCACTATAGG (SEQ ID NO: 89)
or /5AmMC6/
TCTAATACGACTCACTATAGG (SEQ ID NO: 93)
conjugated to the 5'
terminus of the primer.
```

The 3' template binding primer region refers to a primer whose 3' portion binds to a template (e.g., during the first annealing step to prime polymerization). The above-mentioned primer design results in the incorporation of the heel sequence in amplification products after the initial priming event. Subsequently, the 5' heel sequence acts as a clamp to even the amplification efficiency across amplicon homologs.

The extraneous heel sequence may be on either the forward primer or the reverse primer or both.

Hence, certain aspects of the present invention contemplate methods for amplifying a nucleic acid target molecule said methods comprising subjecting a nucleic acid template of said nucleic acid target to amplification using forward and reverse primers wherein at least one primer contains a non-primer binding region 5' extraneous nucleotide sequence conjugated to a 3' template binding primer region wherein said extraneous nucleotide sequence is incorporated into an amplification product after initial priming.

As indicated above either the forward or reverse primer may comprise the extraneous sequence or both may carry the sequence. When both carry the extraneous sequence, the heel may be the same or different.

The present invention is particularly applicable to primers that are potentially capable of priming a set of nucleic acid target homologs.

The present invention further contemplates improved methods of amplifying a nucleic acid molecule included within a population of related nucleic acid molecules by amplification with a forward and reverse primer, comprising: selecting one or both of the forward or reverse primers such that one or both contain a non-primer binding region 5' extraneous nucleotide sequence conjugated to a 3' template binding primer region wherein said extraneous nucleotide sequence is incorporated into the amplification production after initial priming.

Hence, reference to a "nucleic acid molecule" includes a family of related nucleic acid molecules such as a group of homolog nucleic acid molecules.

Kits for reducing amplification bias also form part of the present invention.

All scientific citations, patents, patent applications and manufacturer's technical specifications cited or described in this document are incorporated herein by reference in their entirety.

It is understood that unless otherwise indicated, the subject invention is not limited to specific reagents, process steps, or applications or the like, as such may vary. It is also to be understood that the terminology used herein is for the purpose of describing particular embodiments only and is not intended to be limiting.

Terms and symbols of nucleic acid chemistry, biochemistry, genetics, and molecular biology used herein follow those of standard treatises and texts in the field, e.g., Kornberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein Ed, *Oligonucleotides and Analogs: A Practical Approach* (Oxford University Press, New York, 1991); Gait Ed, *Oligonucleotide Synthesis: A Practical Approach* (IRL Press, Oxford, 1984); and the like.

"Amplicon" means the product of a polynucleotide amplification reaction. That is, it is a population of polynucleotides, usually but not necessarily double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to PCR linear polymerase reactions, NASBAs, rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "Taqman" or "Taq" [registered trade marks] probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese Patent Publ. No. JP 4-262799 (rolling circle amplification); and the like.

An amplification reaction may be a "real-time" amplification where detection chemistry permits a reaction product to be measured as the amplification reaction progresses.

The present invention is particularly concerned with reducing amplification bias across a range of related or homolog nucleic acid molecules. Examples of homolog nucleic acid molecules include viral homologs, polymorphisms, related cancer cells, bacterial homologs, stem cell homologs amongst many others. One aspect of the present invention is the selection of primers at potential points of difference between the homologs. The primers are proposed to carry a non-primer binding region 5' extraneous nucleotide sequence conjugated to a 3' template binding primer region which is incorporated into an amplification product after initial priming.

The heel or 5' extraneous sequence may be from about 1 to about 400 bases in length and all combinations and subcombinations thereof. Preferably the heel is from about 3 to about 100, more preferably from about 4 to about 80 bases in length, still more preferably from about 5 to about 40, yet more preferably about 5 to about 25, with about 10 to about 20 even more preferred.

In effect, the 5' extraneous sequence optionally has a level of complementarity to the target sequence, and it does not contribute substantially to the initial primer binding steps. It is desirable for the heel to have less than 95% complementarity to the core primer. Additional examples of the levels of complementarity can include less than 90%, 85%, 80%, 75%, 70%, 65%, and 60%. Complementarity is determined using standard algorithms.

As used herein, the term "amplifying" means performing an amplification reaction. A "reaction mixture" or "reaction vessel" means a solution or compartment containing all the necessary reactants for performing a reaction, which may include, but not be limited to, buffering agents to maintain pH at a selected level during a reaction, salts, co-factors, scavengers, and the like.

"Complementary or substantially complementary" refers to the hybridization or base pairing or the formation of a duplex between nucleotides or nucleic acids, such as, for instance, between the two strands of a dsDNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when, for example, a DNA strand hybridizes under selective hybridization conditions to its complement. Typically, selective hybridization occurs when there is at least about 65% complementary over a stretch of at least 14 to 25 nucleotides, preferably at least about 75%, more preferably at least about 90% complementary. See, Kanehisa *Nucleic Acids Res.* 12:203, 1984, incorporated herein by reference in its entirety.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick base pairing with a nucleotide in the other strand.

"Genetic locus," or "locus" in reference to a genome or target polynucleotide, means a contiguous subregion or segment of the genome or target polynucleotide. As used herein, genetic locus, or locus, may refer to the position of a gene or portion of a gene in a genome, or it may refer to any contiguous portion of genomic sequence whether or not it is within, or associated with, a gene. Preferably, a genetic locus refers to any portion of genomic sequence from a few tens of nucleotides, e.g., 10-30, or 10-100, in length, to a few hundred nucleotides, e.g., 100-1000 or 100-500 in length, to a few thousands of nucleotide in length, e.g., 1000-10,000 or 1000-3000 in length. In some contexts, genetic loci may refer to the location of a nucleotide within a genome.

"Kit" refers to any delivery system for delivering materials or reagents for carrying out a method of the instant invention. In the context of reaction assays, such delivery systems include systems that allow for the storage, transport, or delivery of reaction reagents (e.g., probes, enzymes, etc., in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes. The kits may also contain compartments adapted to contain the reagents. In one example, a compartment comprises a solid matrix having oligonucleotides or primers or polynucleotides immobilized thereon which participate in the amplification reaction. An example of a solid matrix is a microarray. A kit, therefore, may be part of an overall amplification system having a reagent component, a nucleic acid component, a hardware component and an instructional component.

"Microarray" refers to a solid phase support having a planar surface, which carries an array of nucleic acids, each member of the array comprising identical copies of an oligonucleotide or polynucleotide immobilized to a spatially defined region or site, which does not overlap with those of other members of the array; that is, the regions or sites are spatially discrete. Spatially defined hybridization sites may additionally be "addressable" in that its location and the identity of its immobilized oligonucleotide are known or predetermined, for example, prior to its use. Typically, the oligonucleotides or polynucleotides are single stranded and are covalently attached to the solid phase support, usually by a 5'-end or a 3'-end. The density of non-overlapping regions containing nucleic acids in a microarray is typically greater than 100 per $cm^2$, and more preferably, greater than 1000 per $cm^2$. Microarray technology is disclosed in the following references that are incorporated by reference in its entirety: Schena, Ed, *Microarrays: A Practical Approach* (IRL Press, Oxford, 2000); Southern, *Current Opin. Chem. Biol.,* 2:404-410, 1998.

A "random microarray" refers to a microarray whose spatially discrete regions of oligonucleotides or polynucleotides are not spatially addressed. That is, the identity of the attached oligonucleotides or polynucleotides is not discernable, at least initially, from its location. In one aspect, random microarrays are planar arrays of microbeads wherein each microbead has attached a single kind of hybridization tag complement, such as from a minimally cross-hybridizing set of oligonucleotides. Likewise, after formation, microbeads, or oligonucleotides thereof, in a random array may be identified in a variety of ways, including by optical labels, e.g., fluorescent dye ratios or quantum dots, shape, sequence analysis, or the like.

"Nucleoside" as used herein includes the natural nucleosides, including 2'-deoxy and T-hydroxyl forms, e.g., as described in Kornberg and Baker, *DNA Replication,* 2nd Ed. (Freeman, San Francisco, 1992).

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al, (Eds), PCR: *A Practical Approach and PCR2: A Practical Approach* (IRL Press, Oxford, 1991 and 1995, respectively). For example, in a conventional PCR using Taq DNA polymerase, a double stranded target nucleic acid may be denatured at a temperature >90° C., primers annealed at a temperature in the range 35-90° C. The term "PCR" encompasses derivative forms of the reaction, including but not limited to, RT-PCR, real-time PCR, nested PCR, quantitative PCR, multiplexed PCR, enhanced solid phase PCR, and the like. For further detail of enhanced solid phase PCR, see, for example, Park, et al., Analytical Biochemistry, 375 (2008), pp. 391-393, the entirety of which is incorporated herein by reference in its entirety. The use of enhanced solid phase PCR is preferred in certain embodiments of the present invention for the generation and/or amplification of nucleic acid molecules related to, for example HPV strains. Still more preferred is the use of one or more forward/reverse primer pairs noted herein in enhanced solid phase PCR amplification of nucleic acid molecules related to HPV strains.

Using the ESP-PCR format, 5-prime phosphates are optional since single stranded amplicon is not required as a final PCR product. The 5-prime amine functional groups are also optional in this format and may be used as a preferred means of labelling with a fluorophore for signal generation. However, many alternative means of signal generation may also be employed where there is no requirement for any functional group or an alternative functional group. For example, PCR primers may be non-fluor labelled, and separate 'signal oligonucleotides', which are conjugated with a signal, may be employed. In another example, using ESP-PCR format, all 'aqueous' PCR primers may be used without functional groups and the signal could alternatively be introduced by means of labelled nucleotide analogue incorporation. In other embodiments using ESP-PCR format, all 'aqueous' PCR primers may be used without functional groups, and the signal could be introduced by means of labelled solid support primer such that signal increases in the context of double stranded product.

Alternative means for the generation of single stranded amplicon include conversion of double stranded DNA to single stranded DNA by separating the strands or by removing one strand of the duplex. Strands of the duplex can be separated by thermal or chemical means of disrupting interstrand bonds. Removal of one strand permits recovery of the desired strand and elimination of its complement e.g., Nikiforov et al. (U.S. Pat. No. 5,518,900), who described modifying one of two primers used for amplification by incorporation of phosphorothiate nucleotide derivatives in the 5' end of the modified primer, rendering it resistant to exonuclease digestion. After amplifying target sequences using the polymerase chain reaction (PCR), the dsDNA is subjected to exonuclease digestion. The unprotected strand is preferentially digested by a 5' to 3' exonuclease, leaving a single-stranded product consisting of the other strand. Similar strategies have used exonuclease-resistant branched primers (Shchepinov et al., *Nuc. Acids. Res.* 25:4447-4454 1997) or 5' phosphate-bearing substrate preference of Lambda exonuclease (Higuchi et al., *Nucl. Acids Res.* 25:5685, 1989)

Asymmetric PCR (Gyllensten and Erlich, *Proc. Natl. Acad. Sci. USA* 85:7652-7656 1998; U.S. Pat. No. 5,066,584) generates ssDNA during thermocycling by employing an imbalanced primer pair concentration such that one primer is at a limiting concentration. This favours ssDNA product primed by the primer in excess.

Competitor primer asymmetric PCR (Gillespie, 1997; U.S. patent application Ser. No. 08/628,417) employs the separate addition of competitor primer following PCR thermocycling and prior to further thermocycling to generate ssDNA. Kaltenboeck et al., *Biotechniques* 12:164-171, 1992 described a method of producing ssDNA by initially performing a PCR to generate dsDNA, followed by a separate reaction using the product of the first PCR as a template for a second linear amplification employing one primer. See also U.S. Pat. No. 6,887,664 for examples of Asynchronous PCR.

Reaction volumes range from a few hundred nanoliters, e.g., 200 mL, to a few hundred µL, e.g., 200 µL. "Reverse transcription PCR," or "RT-PCR," means a PCR that is preceded by a reverse transcription reaction that converts a target RNA to a complementary single stranded DNA, which is then amplified, e.g., Tecott et al, U.S. Pat. No. 5,168,038, which patent is incorporated herein by reference in its entirety. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference in its entirety. Detection chemistries for real-time PCR are reviewed in Mackay et al, *Nucleic Acids Research*, 30:1292-1305, 2002, which is also incorporated herein by reference in its entirety. "Nested PCR" means a two-stage PCR wherein the amplicon of a first PCR becomes the sample for a second PCR using a new set of primers, at least one of which binds to an interior location of the first amplicon.

It is proposed that the initial priming events be made with forward and reverse primers where one or both carry a non-primer binding region 5' extraneous nucleotide sequence conjugated to a 3' template binding primer region wherein the extraneous nucleotide sequence is incorporated into an amplification product after initial priming.

The use of non-primer binding region 5' heel sequence conjugated to a 3' template binding primer region as the primer design results in the incorporation of the heel sequence in amplification products after the initial primer binding event. Subsequently, the 5' heel sequence acts as a clamp to even the amplification efficiency across homologs. As such, amplification bias is restricted to initial primer binding events. The "heel clamp" can be placed on either or both forward and reverse primers depending on requirement. There is great freedom of design regarding what sequence the "heel clamp" sequence was comprised to suit the particular application. The 3' template binding primer sequence could take the form of degenerate sequence, consensus sequence, or a hybrid of consensus and degenerate sequences. A pool of exact matching sequences of interest could also be employed. In all these cases the 5' "heel clamp" principle can be employed.

"Polynucleotide" and "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like.

Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or PCRs, employing two or more primers. Guidance for selecting the lengths and sequences of primers for particular applications is well known to those of ordinary skill in the art, as evidenced by the following references that are incorporated by reference in its entirety: Dieffenbach (Ed), *PCR Primer: A Laboratory Manual, 2nd Edition* (Cold Spring Harbor Press, New York, 2003).

"Sample" means a quantity of material from a biological, environmental, medical, or patient source in which detection or measurement of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

Hence, some aspects of the present invention provide methods for amplifying a nucleic acid target molecule, comprising: subjecting a single stranded template of said nucleic acid target to amplification using forward and reverse primers wherein at least one primer contains a non-primer binding region 5' extraneous nucleotide sequence conjugated to a 3' template binding primer region wherein said extraneous nucleotide sequence is incorporated into an amplification product after initial priming.

Other aspects of the present invention contemplate improved methods of amplifying a nucleic acid molecule including within a population of related nucleic acid molecules by amplification with a forward and reverse primer, comprising: selecting one or both of the forward or reverse primers such that one or both contain a non-primer binding region 5' extraneous nucleotide sequence conjugated to a 3' template binding primer region wherein said extraneous nucleotide sequence is incorporated into the amplification production after initial priming.

Examples of heel sequences include:

```
T7a promoter sequence 25-mer:
AAT TCT AAT ACG ACT CAC TAT AGG G
(SEQ ID NO: 95);

M13/pUC Sequencing Primer (-40)
GTT TTC CCA GTC ACG AC (SEQ ID NO: 96);

M13/pUC sequencing primer (-20), 17-mer
GTA AAA CGA CGG CCA GT (SEQ ID NO: 97);

M13/pUC reverse sequencing primer (-26), 17-mer
CAG GAA ACA GCT ATG AC (SEQ ID NO: 98);

M13/pUC sequencing primer (-40), 17-mer
GTT TTC CCA GTC ACG AC (SEQ ID NO: 96);

M13/pUC sequencing primer (-46), 22-mer
GCC AGG GTT TTC CCA GTC ACG A
(SEQ ID NO: 99);

M13/pUC reverse sequencing primer (-46), 24-mer
GAG CGG ATA ACA ATT TCA CAC AGG
(SEQ ID NO: 100);

SP6 promoter sequencing primer, 18-mer
ATT TAG GTG ACA CTA TAG (SEQ ID NO: 101);

SP6 promoter sequencing primer, 24-mer
CAT ACG ATT TAG GTG ACA CTA TAG
(SEQ ID NO: 102);

T7 promoter sequencing primer, 20-mer
TAA TAC GAC TCA CTA TAG GG
(SEQ ID NO: 103);

T3 promoter sequencing primer, 17-mer
ATT AAC CCT CAC TAA AG (SEQ ID NO: 104);
and, T3 promoter sequencing primer, 24-mer
GCG CGA AAT TAA CCC TCA CTA AAG
(SEQ ID NO: 105).
```

Amplification from primer sites such as those described above effectively allows the use of a "universal" primer set, which bind at C and C' to amplify X from a range of strains of the analyte. Furthermore, it should be noted that the amplicon amplified using the universal primers may comprise both conserved and variable regions.

In some embodiments, primers are used which amplify HPV sequences. More preferably these primers are GP5+ is 5' TTT GTT ACT GTG GTA GAT ACT AC 3'(SEQ ID NO: 13) and GP6+ is 5' GAA AAA TAA ACT GTA AAT CAT ATT C 3'(SEQ ID NO: 14). These primers generate an amplicon from HPV which comprises both a conserved region (defined as Y in FIG. 2), and a region which is variable among different strains of HPV (defined as X in FIG. 2).

In other embodiments, these primers are GP5d2+ is 5' TTT KTT ACH GTK GTD GAT ACH AC 3' (SEQ ID NO: 21) and T7aGP6d+ is 5' AAT TCT AAT ACG ACT CAC TAT AGG GGA AAH ATA AAY TGY AAD TCA TAY TC 3' (SEQ ID NO: 22).

In another embodiment, these primers are GP5d3+ is 5' 5Phos TTT GTT ACH GTD GTD GAY ACH AC 3'(SEQ ID NO: 27) and T7aGP6d+* is 5' /5AmMC6/AAT TCT AAT ACG ACT CAC TAT AGG GGA AAH ATA AAY TGY ARD TCA WAY TC 3' (SEQ ID NO: 24).

In other embodiments, the forward primers of a primer pair are selected from the group consisting of

```
TR TTT GTT ACT GTK GTD GAT ACY A,
(SEQ ID NO: 1), optionally
having a caatcagc or /5Phos/caatcagc conjugated
to the 5' terminus of the primer;

CAR YTR TTT GTT ACT GTK GTD GAT A,
(SEQ ID NO: 2), optionally
having a acaat or /5Phos/acaat conjugated to
the 5' terminus of the primer;

CAR YTR TTT GTT ACT GTK GTD GA
(SEQ ID NO: 3), optionally
having a acaat or /5Phos/acaat conjugated to
the 5' terminus of the primer;
```

```
AAY CAR YTR TTT GTT ACT GTK GT
(SEQ ID NO: 4), optionally
having a ggaac or /5Phos/ggaac conjugated to
the 5' terminus of the primer;

TTT GTT ACT GTK GTD GAT ACY AC HCG
(SEQ ID NO: 5), optionally
having a cagctt or /5Phos/cagctt conjugated to
the 5' terminus of the primer;

TTT GTT ACT GTK GTD GAT ACY AC HCG YAG
(SEQ ID NO: 6),
optionally having a a cagctt /5Phos/cagctt
conjugated to the 5' terminus of the primer;

GTK GTD GAT ACY AC HCG YAG TAC
(SEQ ID NO: 7), optionally
having a /5Phos/attacc conjugated to the 5'
terminus of the primer;
and GTD GAT ACY AC HCG YAG TAC HAA
(SEQ ID NO: 8), optionally
having a attacc or /5Phos/ctgtt conjugated to
the 5' terminus of the primer;
and
``` the reverse primers of a primer pair are selected from the group consisting of:

```
TGA AAA ATA AAY TGY AAA TCA TAT TCY TCM MCA TG
(SEQ ID NO: 9),
optionally having a actcactatagg (SEQ ID NO: 87) or
/5AmMC6/actcactatagg (SEQ ID NO: 91)
conjugated to the 5' terminus of the primer;

CAY ARY TGA AAA ATA AAY TGY AAA TC
(SEQ ID NO: 10), optionally
having a aatacgactcactatagg (SEQ ID NO: 88)
or /5AmMC6/ aatacgactcactatagg (SEQ ID NO: 92)
conjugated to the 5' terminus of the primer;

TR CAY ARY TGA AAA ATA AAY TG
(SEQ ID NO: 11), optionally having a
tctaatacgactcactatagg (SEQ ID NO: 89) or /5AmMC6/
tctaatacgactcactatagg (SEQ ID NO: 93)conjugated to
the 5' terminus of the primer;
and TR CAY ARY TGA AAA ATA AA (SEQ ID NO: 12),
optionally having a
aattctaatacgactcactatagg (SEQ ID NO: 90) or /
5AmMC6/
aattctaatacgactcactatagg (SEQ ID NO: 94)
conjugated to the 5'
terminus of the primer.
```

Alternatively, the forward and reverse primers are selected from a group of primers similar to those described hereinabove, but which may differ from the forward or reverse primers described hereinabove by from 0 to about 5 nucleotide substitutions, preferably 0 to about 2 substitutions, at sites where nucleotide substitutions occur between different HPV strains, but with the exclusion of substitutions of the last two nucleotides at the 3' end. The invention also contemplates similar substitutions to optional heel sequences as those for forward or reverse primers described hereinabove, said optional heels conjugated to the 5" terminus of any of the above disclosed forward or reverse primers. In certain preferred embodiments, the forward primer is selected from CAR YTR TTT GTT ACT GTK GTD GA (SEQ ID NO: 3), optionally having a acaat or /5Phos/acaat conjugated to the 5' terminus of the primer and GTD GAT ACY AC HCG YAG TAC HAA (SEQ ID NO: 8), optionally having a ctgtt or/5Phos/ctgtt conjugated to the 5' terminus of the primer. In certain other preferred embodiments, the reverse primer is selected from TGA AAA ATA AAY TGY AAA TCA TAT TCY TCM MCA TG (SEQ ID NO: 9), optionally having a actcactatagg (SEQ ID NO: 87) or /5AmMC6/actcactatagg (SEQ ID NO: 91) conjugated to the 5' terminus of the primer and TR CAY ARY TGA AAA ATA AAY TG (SEQ ID NO: 11), optionally having a tctaatacgactcactatagg (SEQ ID NO: 89) or /5AmMC6/tctaatacgactcactatagg (SEQ ID NO: 93) conjugated to the 5' terminus of the primer.

The above descriptions show examples of primer pairs useful in the present invention. Additional primer pairs can be formed by pairing different forward (e.g., GP5+, GP5d2+, etc.) and reverse primers (e.g., GP6+, T7aGP6d+) with one another.

Certain embodiments of the invention are directed to fragments of any of the herein disclosed primers including all combinations and subcombinations of said primer fragments, to a lower limit of about 20-mer 3-prime core fragments of any of the disclosed primers. As used herein, a "fragment" refers to a truncated primer or probe nucleic acid oligomeric sequence formed by deletion of one or more nucleotides from the original primer.

The present invention also contemplates the amplification of control sequences. In one embodiment, the control sequence may include a region of the genome of the subject from which a biological sample is derived. However, the present invention is not in any way limited to these particular control sequences and other control sequences which would be evident to one of skill in the art are also contemplated. Furthermore, the methods of the present invention may also be performed without the amplification of a control sequence.

In some embodiments, the control sequence is amplified from the genome of a human subject using the primers MLC1_F, which comprises the nucleotide sequence 5' TAC ACA CAG GTG TAC ACA GA 3' (SEQ ID NO: 106) and MLC1_R which comprises the sequence 5' ACC AAG TAC TCT ACG TGT TG 3' (SEQ ID NO: 107).

In other embodiments, the control sequence is amplified from the genome of a human subject using the primers mlc1_95f, which comprises the nucleotide sequence 5' GGC ACC CAG ACA TAC AC 3' (SEQ ID NO: 108) and T7 amlc1_275r (Hee1MLCR), which comprises the sequence 5' AAT TCT AAT ACG ACT CAC TAT AGG GGA AAH ATA AAY TGY AAD TCA TAY TC 3' (SEQ ID NO: 30).

Isolated DNA may be amplified using any DNA amplification protocol. A range of exemplary methods for the amplification of DNA which in no way limit the invention are presented in "DNA Amplification: Current Technologies and Applications" (Demidov and Broude Eds., Horizon Bioscience, 2004).

Isolated RNA may be amplified using any RNA methods known in the art and number of RNA amplification technologies have been developed. Two major categories of these are: (i) those that utilise thermal cycling such as RT-PCR and (ii) isothermal assays such as nucleic acid sequence-based amplification (NASBA) (Compton, *Nature* 350:91-92, 1991; Kievits et al., *J. Virol. Methods* 35:273-286, 1991) and transcription-mediated amplification (TMA) (Hill, *J. Clin. Ligand Assay* 19:43-51, 1996). Isothermal assays may be sub-divided, based on whether: (i) they copy and amplify the target sequence, such as TMA, NASBA and self-sustained sequence replication (3SR) (Guatelli et al., *Proc. Natl. Acad. Sci. USA* 87:1874-1878, 1990; Chadwick et al., *J. Virol. Methods* 70:59-70, 1998; for review see Chan and Fox, *Rev. Med. Microbiol.* 10:185-196, 1999), or (ii) they generate a target-dependent signal which can be further amplified, e.g., invader assays (Lyamichev et al., *Nat. Biotechnol.* 17:292-296, 1999; Ryan et al., *Mol. Diagn.* 4:135-144, 1999). There are various other amplification technologies that do not fit readily into these categories, such as Q beta replicase (Lizardi et al., *Biotechnology* 6:1197-1202, 1988) and branched DNA (Todd et al., *J. AIDS Hum. Retrovirol.* 10: S35-S44, 1995; Pawlotsky et al., *J. Virol. Methods* 79:227-235, 1999). However, it should be understood that the present invention contemplates any method of RNA amplification that would be evident to one of skill in the art. Furthermore, it should be understood that the present invention also contemplates the use of reverse transcriptase or a functional equivalent thereof to convert RNA to DNA which may then be subsequently amplified.

In accordance with the present invention, the amplicons recited at steps (iii) and/or (iv) of the methods described supra are labelled. The amplicons of the present invention may be labelled using any convenient means. Exemplary methods include both pre- and post-synthesis methods. Pre-synthesis labelling methods include labelling of a' PCR primer that is subsequently used for amplification of, and thereby incorporated into, an amplicon via PCR. In this method, the label is typically attached to the 5' end of a primer suitable for the amplification of the amplicon, although labelling at other positions within the primer, such as 3' labelling or non-terminal labelling, is also contemplated.

A chemical linker may also be used between the label and the polynucleotide which is labelled. Appropriate linker sequences will be readily ascertained by those of skill in the art, and are likely to include linkers such as $C_6$, $C_7$ and $C_{12}$ amino modifiers and linkers comprising thiol groups. As will be readily ascertained, a primer may comprise the linker and label, or the linker alone, to which the label may be attached at a later stage.

Post-amplification labelling methods include nick-labelling systems wherein a labelled polynucleotide is synthesised from the amplicon using Klenow polymerase, or a functional equivalent thereof, from random primers. Labelled nucleotides, or nucleotides comprising a linker group, may be incorporated into the Klenow polymerase synthesised polynucleotide during synthesis.

In any event, other labelling methods should be readily evident to one of skill in the art and it should be understood that the present invention is in no way defined or limited by the choice of labelling method.

Preferably, the label used is a "fluorescent marker" or "fluorophore". Many different fluorescent markers will be familiar to those of skill in the art, and the choice of fluorescent marker in no way limits the invention. In other preferred embodiments of the present invention the fluorescent markers of the present invention comprise any fluorescent marker that can be attached to a polynucleotide and which is excitable using a light source selected from the group below:
(i) Argon ion lasers: comprise a blue, 488 nm line, which is suitable for the excitation of many dyes and fluorochromes that fluoresce in the green to red region. Tunable argon lasers are also available that emit at a range of wavelengths (458 nm, 488 nm, 496 nm, 515 nm and others).
(ii) Diode lasers: have an emission wavelength of 635 nm. Other diode lasers which are now available operate at 532 nm. Interestingly, this wavelength excites propidium iodide (PI) optimally. PI staining is widely used for DNA analysis, live/dead counting and ploidy determination. Blue diode lasers emitting light around 476 nm are also available
(iii) HeNe gas lasers: operate with the red 633 nm line.
(iv) HeCd lasers: operate at 325 nm.
(v) 100 W mercury arc lamp: the most efficient light source for excitation of UV dyes like Hoechst and DAPI.

In more preferred embodiments of the present invention the fluorescent markers are selected from: hydroxycoumarin, aminocoumarin, methoxycoumarin, cascade blue, Lucifer yellow, NBD, Phyccerythrin (PE), PerCP, allophycocyanin, Hoechst 33342, DAP1, SYTOX Blue, Hoechst 33258, chromomycin A3, mithramycin, YOYO-1, SYTOX green, SYTOX orange, 7-AAD, acridine orange, TOTO-1, To-PRO-1, thiazole orange, TOTO-3, TO-PRO-3, LDS 751, Alexa Fluor dyes including Alexa Fluoro-350, -430, -488, -532, -546, -555, -556, -594, -633, -647, -660, -680, -700 and -750; BoDipy dyes, including BoDipy 630/650 and BoDipy 650/665; CY dyes, particulary Cy2, Cy3, Cy3.5, Cy5, Cy5.5 and Cy7; 6-FAM (Fluorescein); PE-Cy5, PE-Cy7, Fluorescein dT; Hexachlorofluorescein (Hex); 6-carboxy-4',5'-dichloro-2',7'-dimethoxyfluorescein (JOE); Oregon green dyes, including 488-X and 514; Rhodamine dyes, including X-Rhodamine, Lissamine Rhodamine B, Rhodamine Green, Rhodamine Red and ROX; TRITC, Tetramethylrhodamine (TMR); Carboxytetramethylrhodamine (TAMRA); Tetrachlorofluorescein (TET); Red 6B, Fluor X, BODIPY-FL, SYBR Green I dye, and Texas Red. In particularly preferred embodiments of the present invention, the marker is Cy5 which is particularly convenient for practice of the present invention.

However, in alternate embodiments of the invention, radioactive or non-radioactive labels may be used to label the amplicon. Convenient radioactive labels include $^{32}P$ and $^3H$. These labels may be incorporated into the amplicon and/or primer using any convenient means. A range of non-radioactive labelling methods may also be used. Exemplary non-radioactive labelling methods which in no way limit the present invention are presented in Speel (*Histochem. Cell Biol.* 112:89-113, 1999).

The term "reactant" as used herein should be understood to comprise a polynucleotide immobilized to a bead. More particularly, each reactant comprises a polynucleotide comprising a sequence which is complementary to an amplicon generated according to the methods described herein, which is bound or otherwise associated with a physiochemically distinguishable bead. A reactant may also comprise a sequence which is complementary to a control sequence as hereinbefore defined, i.e., a sequence amplified from the genome of a multicellular organism (Z) or the amplicon of a nucleotide sequence which is conserved among strains of the analyte (Y).

Accordingly, a beadset of reactants may comprise:

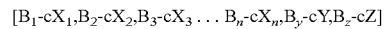

wherein:
$B_1 \ldots B_n$, $B_y$, $B_z$ are each physiochemically distinguishable beads;
$cX_n$ is a polynucleotide immobilized to a bead wherein said polynucleotide comprises a nucleotide sequence which is complementary to a particular nucleic acid sequence which is specific to an analyte or a particular strain of a subject analyte and wherein n is the number of analytes or particular strains of a subject analyte to be detected using the beadset;
cY is an optional member of the beadset and is a polynucleotide immobilized to a bead wherein said polynucleotide comprises a nucleotide sequence which is complementary to a sequence which is conserved among the analytes or strains of a subject analyte;
cZ is an optional member of the beadset and is a polynucleotide immobilized to a bead wherein said polynucleotide comprises a nucleotide sequence which is complementary to a control sequence which is amplified from a multicellular subject.

Preferably, the subject analyte is HPV and the control DNA sequence is a human genomic DNA sequence.

By "complementary", it is to be understood that the immobilized polynucleotide of the reactant should hybridize to an amplicon generated according to the methods described herein under low stringency conditions. Preferably the immobilized polynucleotide should bind to the sample and standard under medium stringency conditions, and most preferable the immobilized polynucleotide should bind to the sample and standard under high stringency conditions.

Reference herein to low stringency includes and encompasses from at least about 0 to at least about 15% v/v formamide (including 1%, 2%, 3%, 4%, 5%, 6%, 7%, 8%, 9%, 10% 11%, 12%, 13% and 14% v/v formamide) and from at least about 1 M to at least about 2 M salt for hybridization, and at least about 1 M to at least about 2 M salt for washing conditions. Generally, low stringency is at from about 25-30° C. to about 52° C., such as 25, 26, 27, 28, 29, 30, 31, 32, 33, 34, 35, 36, 37, 38, 39, 40, 41, 42, 43, 44, 45, 46, 47, 48, 49, 50, 51 and 52° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide, including 16%, 17%, 18%, 19%, 20%, 21%, 22%, 23%, 24%, 24%, 26%, 27%, 28%, 29% and 30% v/v formamide, and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C) % (Marmur and Doty, *J. Mol. Biol.* 5:109, 1962). However, the $T_m$ of a duplex DNA decreases by 1° C. with every increase of 1% in the number of mismatch base pairs (Bonner and Laskey, *Eur. J. Biochem.* 46:83, 1974). Formamide is optional in these hybridization conditions. Accordingly, particularly preferred levels of stringency are, defined as follows: low stringency is 6×SSC buffer, 0.1% w/v SDS at 25-42° C.; a moderate stringency is 2×SSC buffer, 0.1% w/v SDS at a temperature in the range 20° C. to less than 65° C.; high stringency is 0.1×SSC buffer, 0.1% w/v SDS at a temperature of at least 65° C.

The beads, $B_1 \ldots B_n$, $B_y$, $B_z$, of the reactant beadsets are each physiochemically distinguishable beads. The term "physiochemically distinguishable" refers to any physical or chemical characteristic which allows one bead, e.g., $B_1$ to be differentiated from another bead e.g., $B_2$. Accordingly, the physiochemically distinguishable beads allow differentiation of particular reactants.

In certain preferred embodiments the bead comprises a "microparticle". As will be evident to those of skill in the art, almost any material, homogeneous or otherwise may be used for the microparticle. The microparticles contemplated herein may also comprise more than one substance, and as such may comprise shells, alloys or mixtures of organic and/ or inorganic substances. Particularly useful materials which may be used in accordance with the present invention and which represent preferred embodiments of the present invention include materials selected from the list consisting of: silica (for example: quartz or glass), latex, titania, tin dioxide, yttria, alumina, and other binary metal oxides (such as ZnO), perovskites and other piezoelectric metal oxides (such as $BaTiO_3$), ZnS, sucrose, agarose and other polymeric beads. In a particularly preferred embodiment, the microparticle comprises silica.

In some preferred embodiments, the term "physiochemically distinguishable" refers to a measurable difference in any of bead size, the presence or absence of a particular optically detectable label and/or the intensity of an optically detectable label.

Beads contemplated by the present invention may be produced in any convenient regular or irregular 3-dimensional shape. However, it is generally practical to synthesize small spheres or spheroidal particles. Such spheres or spheroidal particles are also referred to herein as "beads". Accordingly, in preferred embodiments of the present invention, the "microparticles" of the present invention are substantially spherical or spheroidal or comprise a "microsphere".

Although the beads of the present invention may be referred to as "microspheres" the actual size of the particles depends on a variety of factors and the particles may or may not actually comprise measurements in the micrometer range. In some preferred embodiments, the bead comprises a diameter (or equivalent measurement in a non-spheroidal particle) of about 300 nm to about 30 μm, including 300 nm, 350 nm, 400 nm, 450 nm, 500 nm, 550 nm, 600 nm, 650 nm, 700 nm, 750 nm, 800 nm, 850 nm, 900 nm, 950 nm, 1.0 μm, 1.1 μm, 1.2 μm, 1.3 μm, 1.4 μm, 1.5 μm, 1.6 μm, 1.7 μm, 1.8 μm, 1.9 μm, 2.0 μm, 2.1 μm, 2.2 μm, 2.3 μm, 2.4 μm, 2.5 μm, 2.6 μm, 2.7 μm, 2.8 μm, 2.9 μm, 3.0 μm, 3.1 μm, 3.2 μm, 3.3 μm, 3.4 μm, 3.5 μm, 3.6 μm, 3.7 μm, 3.8 μm, 3.9 μm, 4.0 μm, 4.1 μm, 4.2 μm, 4.3 μm, 4.4 μm, 4.5 μm, 4.6 μm, 4.7 μm, 4.8 μm, 4.9 μm, 5.0 μm, 5.1 μm, 5.2 μm, 5.3 μm, 5.4 μm, 5.5 μm, 5.6 μm, 5.7 μm, 5.8 μm, 5.9 μm, 6.0 μm, 6.1 μm, 6.2 μm, 6.3 μm, 6.5 μm, 6.6 μm, 6.7 μm, 6.8 μm, 6.9 μm, 7.0 μm, 7.1 μm, 7.2 μm, 7.3 μm, 7.4 μm, 7.5 μm, 7.6 μm, 7.7 μm, 7.8 μm, 7.9 μm, 8.0 μm, 8.1 μm, 8.2 μm, 8.3 μm, 8.4 μm, 8.5 μm, 8.6 μm, 8.7 μm, 8.8 μm, 8.9 μm, 9.1 μm, 9.2 μm, 9.3 μm, 9.4 μm, 9.5 μm, 9.6 μm, 9.7 μm, 9.8 μm, 9.9 μM, 10 μm, 11 μm, 12 μm, 13 μm, 14 μm, 15 μm, 16 μm, 17 μm, 18 μm, 19 μm, 20 μm, 21 μm, 22 μm, 23 μm, 24 μm, 25 μm, 26 μm, 27 μm, 28 μm, 29 μm, 30 μm. More preferably, the bead comprises a diameter (or equivalent measurement in a non-spheroidal particle) of between 1 μm and 10 μm.

In one particularly preferred embodiment, the beads are AmpaSand (Trade mark: Genera Biosystems) beads produced by Genera Biosystems. These beads are commercially available. However, the present invention should not be considered in any way limited to the use of these beads specifically.

The beads may be distinguished on the basis of the presence or absence of one or more "optically detectable labels". Typically, a particular bead may comprise 0, 1, 2, 3, 4, 5 optically detectable labels. As used herein, the term "optically detectable label" refers to any molecule, atom or ion which emits fluorescence, phosphorescence and/or incandescence. Convenient optically detectable labels include those which emit in the ultraviolet (wavelength range of about 350 nm to about 3 nm), visible (wavelength range of about 350 nm to about 800 nm, near infrared (NIR) (wavelength range of about 800 nm to about 1500 nm) and/or infrared (IR) (wavelength range of about 1500 nm to about 10 μm) ranges. However, due to the ease of detection, in one particularly preferred embodiment, the optically detectable label is detectable in the visible wavelength range.

In further preferred embodiments of the subject invention, the optically detectable label comprises one or more labels selected from the list consisting of: a fluorophore, a semiconductor particle, phosphor particle, a doped particle, or a nanocrystal or quantum dot.

In certain particularly preferred embodiments of the present invention, the optically detectable label is a fluorophore. As used herein, the term "fluorophore" refers to any molecule which exhibits the property of fluorescence. For the purposes herein, the term "fluorescence" may be defined as the property of a molecule to absorb light of a particular wavelength and re-emit light of a longer wavelength. The wavelength change relates to an energy loss that takes place in the process. The term "fluorophore" may encompass a range of optically detectable labels such as chemical fluorophores and dyes as well as quantum dots.

Particularly convenient optically detectable labels which may be used in accordance with the present invention are embedded fluorescent particles of semiconductors. These optically detectable label particles may be so small that their properties and emission become size dependent. Such small optically detectable label particles are referred to in the art as semiconductor nanoparticles, quantum dots, quantum wires, quantum rods or nanocrystals or Q-particles. However, as used herein, the term "Quantum Dot" or "QD" is to be understood to encompass all such particles. Furthermore, optically detectable labels comprising QDs may comprise approximately spherical or spheroidal particles, or coated spherical or spheroidal particles. However, the term QD should not be considered in any way to be limited to a spherical, spheroidal, circular, cylindrical or any other morphology of a "dot". For example, as used herein QDs may also comprise other morphologies including, inter alia, rod-like, ellipsoidal, or coated rod-like or ellipsoidal particles.

QDs consist of a nanometer-scale crystalline core of semiconductor material; biologically active versions are typically surrounded by a protective shell and external coat. For example, QDs may comprise semiconductor crystallites which are about 2 nm to about 30 nm in diameter and may contain approximately 50-500,000 atoms within the crystal, including luminescent crystals comprising materials such as ZnS, ZnSe, ZnTe, CdS, CdSe, CdTe, PbS, PbSe, PbTe, HgS, HgSe, HgTe, Si, ZnO.

QDs fluoresce with a broad absorption spectrum and a narrow emission spectrum. Unlike some other fluorophores, which have distinct absorption spectra, QDs absorb light over a wide spectral range, which allows quantum dots to be excited with a range of light sources, such as lasers, arc lamps, or LEDs. Furthermore, a collection of different QDs can be used in multiplex applications using only a single excitation source. However, the emission spectra for each dot is typically very narrow, in the order of about 30 nm, the exact color depending on the particle's diameter and composition. Furthermore, the narrow emission spectrum of QDs permits spectral resolution of adjacent dots. In addition to the benefits above, QDs are also relatively photostable, even during intense excitation, and are brighter than fluorophores.

In light of the foregoing, it should also be understood that the present invention encompasses the use of different sized QDs.

Furthermore, the present invention contemplates QDs which are treated with procedures such as thermal treatment, surface modification, alloying, surface passivation or capping with surface coatings to enable the QD to emit with high quantum yield and to improve the photostability for long periods of time.

QDs are also commercially available from companies such as Quantum Dot Corp. (QDC), which produces QDs such as the Qdot [Trade Mark] 605 streptavidin conjugate, containing a cadmium-selenide core that emits at 605 nm. Qdot conjugates that emit at 525, 565, 585, and 655 nm are also available. However, it should be understood that the present invention is not limited in any way by the particular composition of the QD (or any other optically detectable label) and any QD (commercial or otherwise) may be compatible with the present invention.

There are also many fluorescent dyes that are available in the art which may be used as fluorophores in accordance with the present invention. An important property of a fluorescent dye or other fluorophore, which determines its potential for use is the excitation wavelength of the fluorophore; it must match the available wavelengths of the light source. However, many different fluorescent dyes and other fluorophores will be familiar to those of skill in the art, and the choice of fluorescent marker in no way limits the subject invention. Particularly convenient fluorescent dyes which may be used for the labelling of a substrate include those discussed supra with regard to labelling of the PCR amplicon. However, when choosing fluorescent labels, the emission spectra of the fluorescent label used for the binding agent(s) should be distinct from the emission spectrum of the label used for the amplicon(s).

Two dyeing techniques are commonly used to fluorescently label beads and microspheres—internal dyeing and external dyeing (surface-labelling). The two techniques produce beads with unique properties, each beneficial for different applications. Internal dyeing produces extremely stable particles with typically narrow fluorescence emissions. These beads often display a greater resistance to photobleaching. As the fluorophore is inside the beads, surface groups are available for use in conjugating ligands (proteins, antibodies, nucleic acids, etc.) to the surface of the bead. For this reason, internally labelled beads are typically used in analyte-detection and immunoassay applications. Surface-labelling involves conjugation of the fluorophore to the bead surface. Because the fluorophores are on the surface of the bead, they are able to interact with their environment just as the fluorophores on a stained cell. The result is a bead standard that exhibits the same excitation and emission properties as stained cell samples, under a variety of different conditions, such as the presence of contaminants or changes in pH. The "environmentally responsive" nature of surface-labelled beads makes them ideally suited for mimicking biological samples. Externally labelled beads are frequently used as controls and standards in a number of applications utilizing fluorescence detection. However, the present invention contemplates the association of a bead with a fluorescent label via any means.

The terms "phosphorescent beads", "phosphor beads" and "phosphors" are used interchangeably herein. What constitutes a phosphorescent optically detectable label would be readily understood by one of skill in the art. However, by way of example, which in no way limits the invention, suitable phosphors include small particles of ZnS, ZnS:Cu, Eu oxide and other phosphors used in display devices.

A optically detectable label comprising a "doped bead" may include a particle which comprises occluded amounts of one or more rare earth ions, such as Eu, Y, Yb, Sm and the like.

As used herein, the term "optically detectable label" should be understood to also encompass multiple optically detectable labels, mixtures of optically detectable labels, coated nanocrystals, alloys and other complex mixtures that would be evident to the skilled artisan. The use of all such optically detectable labels is to be considered as being within the scope of the methods and agents described herein.

Furthermore, the optically detectable label of the reactant may comprise an optically detectable label incorporated into the immobilized polynucleotide sequence which is bound or otherwise associated with the bead, rather than being a label directly associated with the bead per se.

The beads are generally labelled by the immobilized "tag" or probe oligonucleotide. This tag carries an internal amine ($NH_2$) which is then modified by conjugation with a succinimidyl ester of a dye. In the current set, the dye used is BODIPY-TMR. By mixing labelled and unlabelled tags and then conjugating this mix to the beads, one can produce classes of beads with different levels of the fluorescent marker. The ratios conveniently used are in a series of $1:5^x$; that is, the different classes are produced by using the ratio of unlabeled: labelled tags. This is generically exemplified below in Table 4.

TABLE 4

Ratio of unlabeled to labeled tags

| Class | Rel amount Unlabeled | Rel Amt Labeled |
|---|---|---|
| All | 0 | All |
| None | All | 0 |
| 1/5 | 5 | 1 |
| 1/25 | 25 | 1 |
| 1/125 | 125 | 1 |

The optically detectable label may be applied to a bead at a range of concentrations or intensities, thereby providing another basis on which particular beads may be "physiochemically distinguishable". For example, if the maximum detectable intensity of the signal of a particular optically detectable is deemed to be 100%, the label may be applied to a range of beads to give intensities of 0%, 2%, 4%, 6%, 8%, 10%, 15%, 20%, 25%, 30%, 35%, 40%, 45%, 50%, 60%, 70%, 80%, 90%, 100%.

In one embodiment, the beadset of reactants comprises beads of 3.0 μm, 3.5 μm, 4.1 μm, 5.0 μm, 5.6 μm and 6.8 μm, wherein the 3.0 μm, 3.5 μm and 4.1 μm diameter beads are labelled at 0% and 100%, the 5.0 μm diameter beads are labelled at 0%, 100% and 20% and the 5.6 μm and 6.8 μm diameter beads are labelled at 0%, 100%, 20% and 4%.

In another embodiment, the beadset of reactants comprises beads of 3.0 μm, 3.5 μm, 3.77 μm, 5.6 μm and 6.8 μm. All bead sizes, (except for the 3.0 μm which is divided by zero level and high level of TMR), are divided according to their respective zero level, medium level, and high level of TMR.

In other embodiments, TMR levels are set such that during bead to oligo conjugation, oligos with defined total oligo to fluor-labelled ratios are used to determine discrete TMR groupings. For example, zero levels of TMR have unlabelled oligos included in conjugation; high levels of TMR have a 3:1 total oligo to fluor-labelled ratio of oligos included in conjugation; and medium levels of TMR have from a 150:1 to an 80:1 total oligo to fluor-labelled ratio of oligos included in conjugation, depending on bead size.

The immobilized polynucleotide component of the reactant, e.g., $cX_n$, cY and/or cZ may be bound to a bead using any convenient means.

The immobilized polynucleotide may be encapsulated in beads during their production or may be attached to their surface post-production. The choice method used to associate the polynucleotide with the bead will depend on the material used, as would be readily ascertained by the skilled artisan. In addition, further treatments, including silanization (coating of the substrate with silanes), may be performed on the beads prior to attachment of the polynucleotide in order to increase the binding of said polynucleotide to the bead.

Generally, beads may be coated with any compound that will covalently attach, or otherwise adsorb, to the surface of the bead, and in addition the reactant should also have a chemical moiety for the attachment of a polynucleotide, such as a thiol, amine or carboxyl group. Non-limiting examples of compounds with these characteristics include amino-terminated silanes such as amino-propyltrimethoxysilane and amino-propyltriethoxysilane, as well as thiol-terminated silanes such as thio-propyltrimethoxysilane and thio-propyltriethoxysilane. In addition to silanes, compounds such as poly-L-lysine that non-covalently attach to the glass surface and electrostatically adsorb the phosphate groups of the polynucleotide are also within the scope of the present invention. Therefore, other compounds, including other silanes suitable for the attachment of a polynucleotide to a surface would be readily identified by the skilled artisan, and the present invention is not limited by the choice of compound.

The polynucleotide can be attached to the bead using any convenient means; typically this is done by physical adsorption or chemical linking. In addition, beads may be further coated with an agent that promotes or increases the adsorption or binding of the polynucleotide to the surface of the bead, such as amino-silanes. However, other agents that perform this function will be readily identified by persons of skill in the art. In some other embodiments, the polynucleotide is covalently conjugated to the bead by an oligo acrydite group reacting with a bead thiol group.

In another embodiment, the nucleic acid molecule is bound to the bead via the Universal Anchoring System (UAS) (Trademark: Genera Biosystems). Briefly, this system involves the use of a "bridge" nucleic acid molecule to ligate a nucleic acid "tag" sequence on the substrate with a target sequence. The "bridge" sequence is partially complementary to the tag sequence and partially complementary to the target sequence, such that the bridge sequence may bind to both the tag and target sequences and hold them in alignment such that the tag and target sequences may be ligated using a ligase. The UAS is also commercially available. However, the present invention should not be considered in any way limited to this particular method of linking a nucleic acid molecule to a substrate.

Determination of whether binding has occurred between an amplicon and a reactant may be done using any methodology which allows localization of a bound amplicon label to a particular physiochemically distinguishable reactant. In a particularly preferred embodiment, flow cytometry is used.

Flow Cytometry may be defined as a technology to measure properties of particles or cells as they move, or flow, in liquid suspension. An analogy may be made with a more familiar item of laboratory equipment, the microscope, to further describe this technology. Most microscopes have the following components:

A Light Source

The typical microscope uses a light bulb to illuminate the object. In the flow cytometer, the light source is often a laser. Lasers are used because they provide a very concentrated and intense beam of monochromatic light. The monochromatic character of the light is especially important in making fluorescence measurements.

The Stage

In a microscope, the stage is movable to allow passage of the object to the viewing field of an objective lens. In the flow cytometer, the cells or particles exist in liquid suspension. The liquid flows in response to air pressure, past an objective lens, thus carrying the cells or particles through the viewing field.

The Lens

In both the microscope and the flow cytometer, the lens collects light from the object.

The Filters

Some microscopes have filters to select those characteristics of the light that are most important to the observer. This is particularly true of fluorescence microscopes. In fluorescence, dye molecules are excited by light of a characteristic wavelength which then produce emitted light of a longer wavelength. The filters remove the excitation light to allow the emission light to be seen or measured.

The Detectors

In a microscope, the light detector is the observer. The flow cytometer uses highly sensitive light detectors called photomultiplier tubes (PMT's). The detectors must be able to measure the brief flashes of emitted light from cells or particles that are moving one at a time through the viewing field of the objective lens at rates of up to several thousand per second.

Most flow cytometers can measure both Light Scatter and Fluorescence.

In certain preferred embodiments, beads are detected and/or sorted according to the methods of the present invention using flow cytometry. The present invention, however, is in no way limited to the particular flow cytometry method or apparatus hereinbefore described. This example was provided only for illustrative purposes, and the present invention is not to be limited to an instrument or method according to the example provided.

Using flow cytometry, the size of a given bead may be determined by the light scatter of the object.

Light scatter is the interaction of light and matter. All materials, including beads, will scatter light. It is composed largely of light that is reflected or refracted. The position from which an object is viewed often determines what can be told about it. In the flow cytometer, light scatter detectors are usually located opposite the laser (relative to the cell or particle), and to one side of the laser, in-line with the fluid-flow/laser beam intersection. The measurements made by these detectors are called forward light scatter and side light scatter, respectively.

Forward light scatter provides some information on the relative size of individual cells or particles, whereas side light scatter provides some information on the relative granularity of individual beads. They are often used in combination to distinguish the different major categories of white cells in unseparated mammalian blood, but are useful in a wide variety of other assays as well, such as the determination of the size of a microparticle.

The present inventors have determined that flow cytometry is able to distinguish between beads of about 3.0 μm, about 3.5 μm, about 4.1 μm, about 5.0 μm, about 5.6 μm and about 6.8 μm in diameter. The present inventors also have determined that flow cytometry is able to distinguish between beads of about 3.0 μm, about 3.5 μm, about 3.77 μm, about 5.0 μm, about 5.6 μm and about 6.8 μm in diameter. Still other bead classes can be distinguished, such as between 5.0 and 5.6 and 5.6 and 6.8. Accordingly, the present inventors have identified that flow cytometry can differentiate up to at least 6 different sizes of beads.

In addition to size detection, flow cytometers typically have one or more lasers and detectors for the detection of fluorescence in a sample. Fluorescence is the property of a molecule to absorb light of a particular wavelength and re-emit light of a longer wavelength. The wavelength change relates to an energy loss that takes place in the process. It is a characteristic that makes fluorescence extremely useful: filters may be used to exclude the excitation light from the light detector or the viewer. Thus, the only light measured or seen originates from the fluorophore. Interference from background or stray light striking the detectors is extremely low.

There are many fluorescent dyes that are useful for flow cytometry. They bind to a variety of cytochemical components, such as nucleic acids; proteins; specific cell-membrane, nuclear, and cytoplasmic receptors; intracellular ion molecules; and many more. A key property of a fluorescent dye which determines it's potential for use in a flow cytometric assay is the excitation wavelength, i.e., it must match the available wavelengths of the light source.

In other aspects, the present invention provides methods for diagnosing an infection by a pathogenic analyte in a subject, said method comprising:
(i) obtaining a biological sample from the subject which putatively comprises said pathogenic analyte;
(ii) isolating nucleic acid from said sample;
(iii) amplifying the nucleic acid from said sample using primers which generate an amplicon which is distinct for said analyte or a particular strain of said analyte;
(iv) optionally amplifying a control nucleic acid sequence from the subject;
(v) optionally effecting labelling of the amplicon(s) recited at steps (iii) and/or (iv);
(vi) hybridizing the labelled amplicon(s) to a beadset of reactants wherein each member of the beadset comprises a nucleic acid molecule having complementarity to a nucleotide sequence of the analyte or a particular strain of the analyte or a control nucleotide sequence, bound or otherwise associated with a physiochemically distinguishable bead; and
(vii) determining to which of the reactants an amplicon has bound;
wherein the association of an amplicon with a particular reactant is indicative of an infection by the analyte in the subject.

In other aspects, the hybridizing occurs in the presence of at least one signal oligonucleotide sequence.

In other aspects, the hybridizing occurs in the presence of at least one blocking oligonucleotide sequence.

As used herein the term "subject" refers to any organism may be susceptible to infection by another analyte. As such, a "subject" includes, but is not limited to animals, plants, fungi and bacteria (which may be infected by bacteriophage). As used herein the term "animal" preferably includes a mammal and more preferably a primate including a lower primate and even more preferably, a human. However, the term "animal" also specifically includes livestock species such as cattle, horses, sheep, pigs, goats and donkeys as well as laboratory animals. Examples of laboratory test animals include mice, rats, rabbits, guinea pigs and hamsters. Rabbits and rodent animals, such as rats and mice, provide a convenient test system or animal model as do primates and lower primates. Non-mammalian animals such as avian species, zebrafish, amphibians (including cane toads) and *Drosophila* species such as *Drosophila melanogaster* are also contemplated.

The "subject" may also be a non-animal such as a plant. The term "plant" specifically includes plants of agricultural value such as cereal plants (e.g., wheat, barley, oats, rye, triticale and maize), rice, fruit trees (e.g., apples, bananas, mangoes and oranges), sugarcane, horticultural crop plants (e.g., potatoes, carrots and onions) and the like.

However, in certain preferred embodiments, the present invention provides methods for diagnosing HPV infection in a human subject, said method comprising:
(i) obtaining a biological sample from the human subject which putatively comprises HPV;

(ii) isolating nucleic acid from said sample;
(iii) amplifying the nucleic acid from said sample using primers which generate an amplicon which is distinct for said analyte or a particular strain of said analyte;
(iv) optionally amplifying a control nucleic acid sequence from the genomic DNA of the human subject;
(v) optionally effecting labelling of the amplicon(s) recited at steps (iii) and/or (iv);
(vi) hybridizing the labelled amplicon(s) to a beadset of reactants wherein each member of the beadset comprises a nucleic acid molecule having complementarity to a nucleotide sequence of HPV or a particular strain of HPV or a control nucleotide sequence, bound or otherwise associated with a physiochemically distinguishable substrate; and
(vii) determining to which of the reactants an amplicon has bound;
wherein the association of an amplicon with a particular reactant is indicative of HPV infection in the human subject.

In other aspects, the hybridizing occurs in the presence of at least one signal oligonucleotide sequence.

In other aspects, the hybridizing occurs in the presence of at least one blocking oligonucleotide sequence.

In some aspects, the present invention also contemplates methods for determining the risk of a human subject developing a disease associated with one or more strains of HPV said method comprising:
(i) obtaining a biological sample from the human subject which putatively comprises HPV;
(ii) isolating nucleic acid from said sample;
(iii) amplifying the nucleic acid from said sample using primers which generate an amplicon which is distinct for said analyte or a particular strain of said analyte;
(iv) optionally amplifying a control nucleic acid sequence from the genomic DNA of the human subject;
(v) optionally effecting labelling of the amplicon(s) recited at steps (iii) and/or (iv);
(vi) hybridizing the labelled amplicon(s) to a beadset of reactants wherein each member of the beadset comprises a nucleic acid molecule having complementarity to a nucleotide sequence of HPV or a particular strain of HPV or a control nucleotide sequence, bound or otherwise associated with a physiochemically distinguishable substrate; and
(vii) determining to which of the reactant an amplicon has bound;
wherein the association of an amplicon with a particular reactant comprising a polynucleotide which is complementary to a strain of HPV associated with a particular disease, is indicative of an increased risk said disease in the subject.

In other aspects, the hybridizing occurs in the presence of at least one signal oligonucleotide sequence.

In other aspects, the hybridizing occurs in the presence of at least one blocking oligonucleotide sequence.

When the labelling of the amplicons as outlined in part (v) occurs, both the amplicons and the beads are labelled.

Exemplary diseases associated with one or more particular strains of HPV include those presented in Table 3. Accordingly, in some aspects, the present invention provides methods for diagnosing an increased risk of a subject developing a particular disease by specifically identifying which strain of HPV is infecting the subject. In certain particularly preferred embodiments, the methods are adapted to determining the risk of a human subject developing cervical cancer.

The present invention further contemplates diagnostic kits for use according to the methods described herein, including diagnosing HPV infection in a human subject and/or assessing the risk of a human subject developing an HPV-associated disease, including cervical cancer. The kits comprise a beadset of reactants which each comprise a polynucleotide which is complementary to a nucleotide sequence of a particular strain of HPV, bound or otherwise associated with a physiochemically distinguishable substrate. Optionally, the kits may also comprise primers that bind to conserved sequences among different strains of HPV, but generate an amplicon which comprises distinct nucleotide sequences for each strain of HPV wherein the amplicon generated is putatively complementary to a polynucleotide bound to or otherwise associated with one or more physiochemically distinguishable beads of the kit.

In some embodiment, the beadsets of reactants comprise at least group of beads, each comprising a diameter of any one of about 3.0 µm, about 3.5 µm, about 4.1 µm, about 5.0 µm, about 5.6 µm and about 6.8 µm. In a further preferred embodiment, each size group of beads comprises one or more subgroups of microspheres each with a fluorescent label at a range of different intensities. The fluorescent label is TMR and can be applied at intensities of about 0%, about 4%, about 20% and about 100%.

In other embodiments, the beadsets of reactants comprises at least group of beads, each comprising a diameter of any one of about 3.0 µm, about 3.5 µm, about 3.77 µm, about 5.0 µm, about 5.6 µm and about 6.8 µm. TMR levels are set such that during bead to oligo conjugation, oligos with defined total oligo to fluor-labelled ratios are used to determine discrete TMR groupings. For example, zero levels of TMR have unlabelled oligos included in conjugation; high levels of TMR have a 3:1 total oligo to fluor-labelled ratio of oligos included in conjugation; and medium levels of TMR have from a 150:1 to an 80:1 total oligo to fluor-labelled ratio of oligos included in conjugation, depending on bead size.

In further embodiments, the kits comprises the primers GP5+ and GP6+ and optionally primers MLC1_F and MLC1_R.

In yet other embodiments, the kits comprise the primers GP5d2+ and T7aGP6d+ and optionally primers mlc1__95f and T7amlc1__275r.

In still other embodiments, the kits comprise the primers GP5d3+ and T7aGP6d+* and optionally primers mlc1__95f and T7amlc1__275r.

The present invention includes additional embodiments of primer pairs wherein the individual forward (e.g., GP5+, GP5d2+, etc.) and reverse primers (e.g., GP6+, T7aGP6d+) described herein are combined with one another.

The kits may also be in the form of solid phase chips or supports, commonly referred to as biochips. All or part of the reagents used in the subject assay may be incorporated into a biochip or miniaturized into a nanoassay. Although flow cytometry is particularly useful in measuring outputs of the subject assay, the biochips may be used to measure or automate other signals such as those associated with whispering gallery mode assays.

Notwithstanding fluorescent intensities in a preferred aspect of the multiplexing method, other forms of identification are encompassed by the present invention. One such alternative method includes whispering gallery mode (WGM) detection. In this embodiment, a fluorescent marker is incorporated into beads of a subset or incorporated or bonded to DNA on the surface of the beads. This fluorescent marker can excite the WGMs with a laser or unfocussed white light source or with filtered unfocussed white light source.

WGMs allow only certain wavelengths of light to be emitted from the particle. The result of this phenomenon is that the usual broad emission (10-100 nm wide) bands from, for example, a fluorophore become constrained and appear as a series of sharp peaks corresponding effectively to standing mode patterns of light within the particle. In accordance with the present invention, it has been determined that the WGM profile is extremely sensitive to changes at the surface of the microspheroidal particle and that the WGM profile changes when the microspheroidal particle interacts with analytes or molecules within its environment.

Accordingly, other aspects of the present invention contemplate methods of detecting an analyte such as an amplicon from an HPV strain comprising a strain-specific sequence, said method comprising contacting at least one set of microspheroidal particles with a sample putatively comprising said analyte, wherein each particle within a set of microspheroidal particles comprises an optically detectable label and an immobilized putative binding partner of said analyte (e.g., a primer or probe capable of binding, capturing or otherwise immobilizing an amplicon from an HPV strain) wherein each particle set has a defined WGM profile, wherein binding of said analyte to said immobilized binding partner results in a change in said WGM profile of said at least one set of microspheroidal particles which is indicative of the presence of said analyte.

The methods of the present invention may be applied to detect modulation in the WGM profile of a microspheroidal particle wherein said modulation results from detection of binding or other association of molecules in a sample to potential binding particles immobilized to the surface of the microspheroidal particle. Detection of binding reactions between an analyte and its binding partner based on sensitive changes in WGM profiles enables the identification and isolation of the analytes.

A feature of the present invention is that the microspheroidal particles may be excited with a wide range of light sources, facilitating measurement in many different WGM profiles.

An "optically detectable label" may be any molecule, atom or ion which emits fluorescence, phosphorescence and/or incandescence. In some other preferred embodiments of the present invention, the optically detectable label is a fluorophore, which may encompass a range of optically detectable labels such as chemical fluorophores and dyes as well as quantum dots.

In some embodiments, the present invention provides at least one microspheroidal particle comprising a latex or silica particle which is 1 µm to 100 µm in diameter, labelled with an optically detectable label, such as a fluorophore or quantum dot, the particle further comprising a putative binding partner of an analyte to be detected. An example is a capture nucleic acid molecule capable of binding to an HPV amplicon generated by the amplification using two primers to a conserved region of the HPV genome which flank a strain-specific region. The optically detectable label is detectable at visible wavelengths and the microspheroidal particle exhibits one or more WGM profiles. One or more of the WGM profiles of the microspheroidal particle detectably modulates when analytes interacts with the immobilized binding partner on the particle. Any such change in WGM profile is indicative of the presence of an analyte which has bound to its binding partner.

Block oligos can be included in with the beads during hybridization of single-stranded amplicon to beads. The block oligos have deliberate points of difference from the corresponding bead-probe binding regions of the single-stranded amplicons. There can be a block oligo for each bead-probe in the mix. The block oligos are intended to act as appropriately pitched filters. In the context of a thermal denaturation followed by slow decrease in temperature, most efficient hybridization events occur first. Type-specific amplicons bind to the matching bead-probe according to type early on. The block oligos can bind to and saturate the bead-probes lower down the thermal profile. This can prevent cross-type hybridization events (where between types there are more points of difference at probe binding regions compared with the block oligos) or other non-specific hybridisations such as other amplicons, including primer-dimer products, from occurring. A block oligo can be present for human control as well as the HPV types. Examples of block oligos are described in Table 2 above. The level of similarity between the block oligos and the complementary sequence to the type-specific bead probe region (for which it is designed to block) can be between 40% and 95%. Another example of the level of similarity is between 75% and 85%.

Signal oligos can be used as alternatives to the use of directly fluor labelled PCR primers for generating signal. Signal oligos are fluor labelled probes that bind to amplicon products at a site different from the bead-probe region to yield a bead-probe/amplicon/signal oligo complex upon hybridization. The advantages of their use would be: to preclude the requirement for fluor-labelling (and excessively handling) PCR primer during production, use of much less fluor-labelled oligo for equivalent sensitivity (and cost benefits), reduction of fluor background such that higher sensitivity can achieved without wash steps (handling and risk benefits), increased sensitivity in the absence of block oligos due to extra level of 'nesting' in the hybridization complex, and potential use of more of PCR product in the 'detection' steps. All of these benefits would facilitate a 'single tube' approach. Examples of signal oligos are described in Table 2 above.

Alternatively, a double stranded DNA-specific dye, such as SYBR Green I dye may be used as a mode of attaching signal to amplicon on bead alongside or instead of signal oligos.

The present invention is further described by the following non-limiting examples.

Example 1

HPV Diagnosis

DNA Isolation and Amplification

An overview of the DNA extraction protocol used to isolate DNA for the HPV diagnostic method is shown in FIG. 1.

Figure 2:
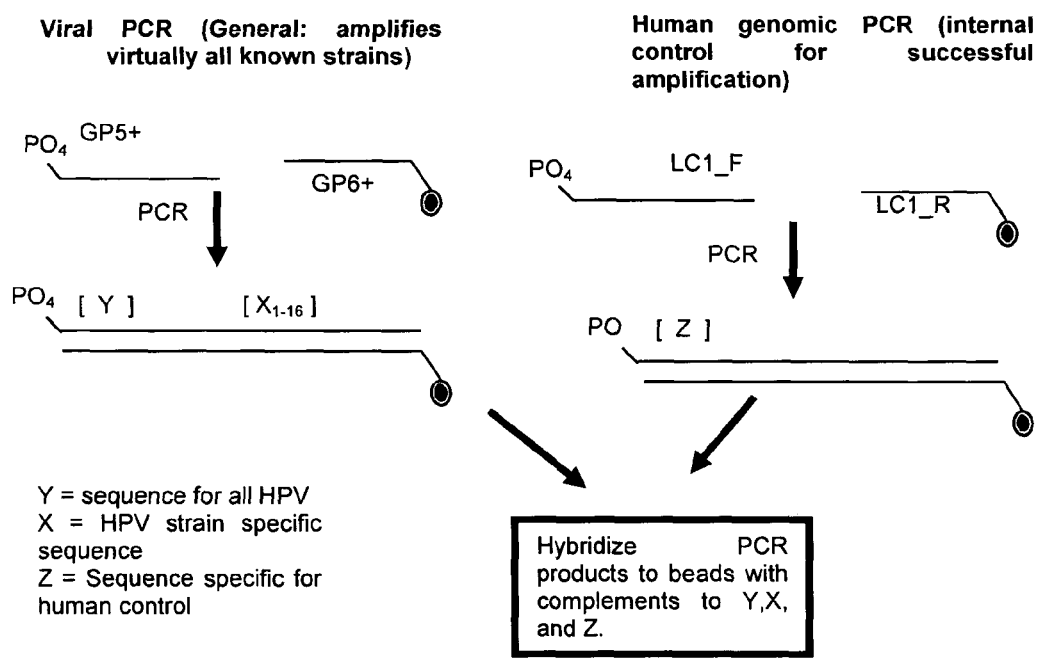
FIG. 2 is a graphical representation showing a PCR protocol that can be used to amplify HPV and human DNA from a DNA sample. GP5+ and GP6+ refer to universal HPV primers which bind to conserved sequences (Y) in HPV and generate an amplicon which comprises a region which is variable between HPV strains ($X_{1-16}$). Primers LC1_F and LC1_R amplify a human genomic DNA region (Z) which serves as a control in the later hybridization steps. Primers GP6+ and LC1_R comprise a fluorescent label which is incorporated into the amplicon generated.
Figure 3:
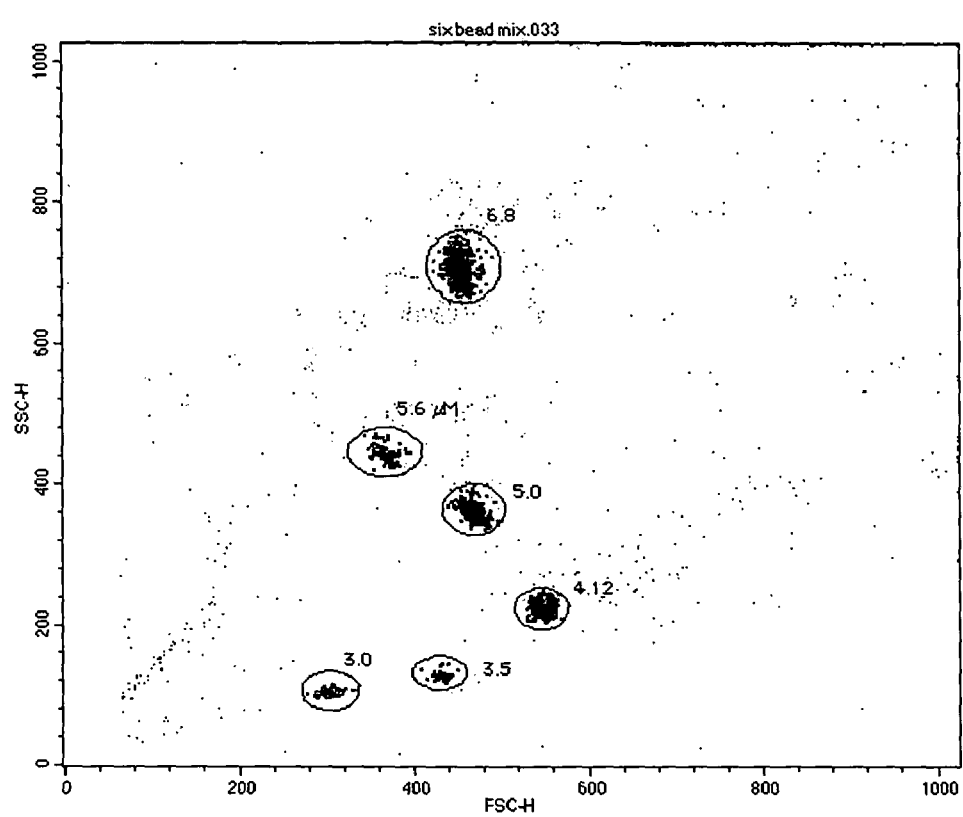
FIG. 3 is a graphical representation showing the differentiation of microspheres on the basis of size. Six clusters corresponding to microspheres comprising diameters of 3.0 μm, 3.5 μm, 4.1 μm, 5.0 μm, 5.6 μm and 6.8 μm are shown.

As shown in FIG. 2, PCR was used to amplify the DNA sample. The primers GP5d2+ and T7aGP6d+ were used to generate an amplicon for any HPV strain which was present in the DNA sample. Primer T7aGP6d+ comprised a fluorescent label, specifically A647 to allow later visualization of the amplicon binding to the binding agents. The viral amplicons generated comprised both a conserved region (Y) which is conserved among all the strains of HPV examined and a region which is variable (i.e., strain-specific) between HPV strains, $X_n$, wherein n represents a variable region associated with each HPV strain. The immobilized binding partners on beads specifically bind to the HPV strain-specific genome.

Also, an amplicon from the human subject genomic DNA was also generated using the mlc1_95f and T7amlc1_275r primers to serve as a control. In this case, primer T7amlc1_275r also carried an A647 label.

Example 2

HPV Diagnosis

Multiplex Detection

The amplicons generated in Example 1 were hybridized to an array of binding agents, each carrying a polynucleotide which is complementary to the variable region of the putative viral amplicon generated from each of HPV strains 6, 11, 16, 18, 31, 33, 35, 39, 45, 51, 52, 56, 58, 59, 67 and 68 ($X_1$ through $X_{16}$). See Table 2 for the nucleotide sequences of the capture nucleic acids immobilized to the beads. Furthermore, the array can optionally comprise a binding agent which comprises a polynucleotide which is complementary to conserved region of the HPV viral amplicons (Y). Finally, a binding agent comprising a polynucleotide which is complementary to the sequence of the human control amplicon is included. The capture nucleic acid may be DNA or RNA. If RNA is used, a reverse transcriptase may be required to generate RNA from the DNA amplicon.

Figure 4:
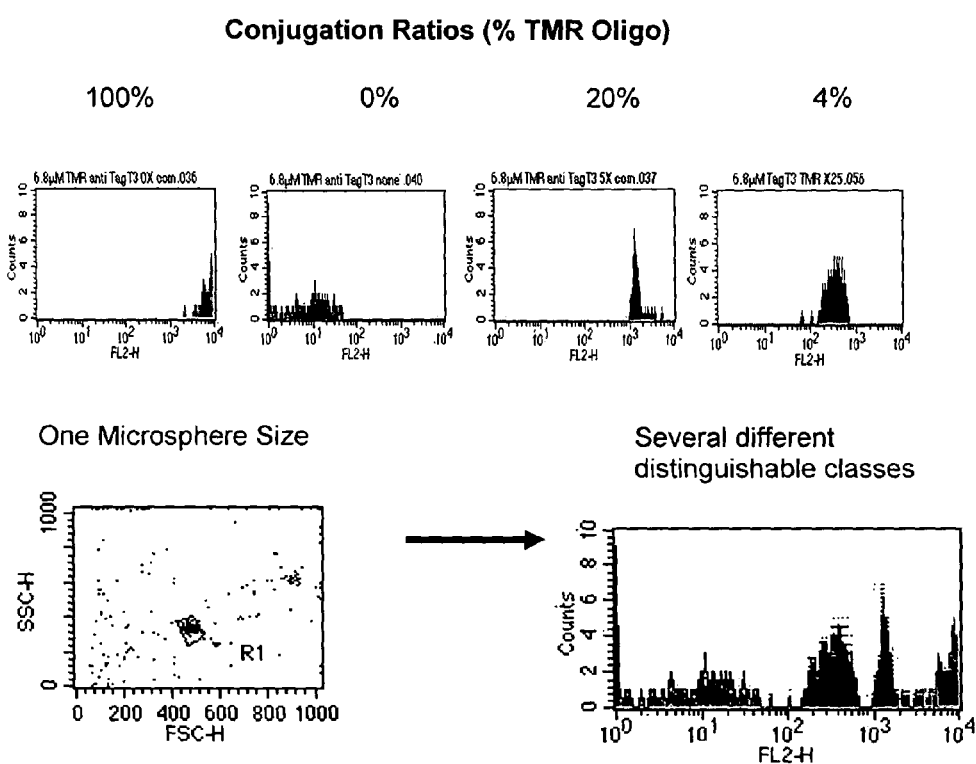
FIG. 4 is a graphical representation showing the differentiation of microspheres of the same size on the basis of fluorescent label intensity. TMR relative intensities of 0%, 4%, 20% and 100% could be clearly distinguished.
Figure 7:
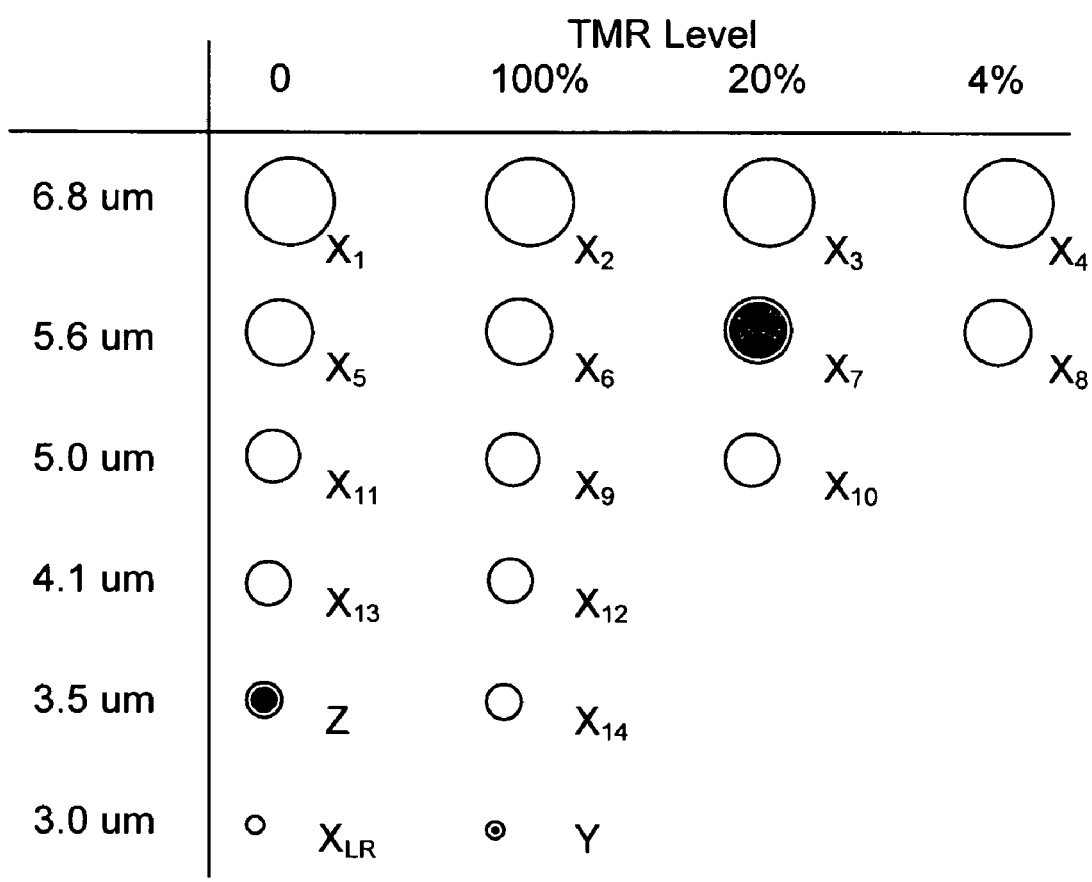
FIG. 7 is a graphical representation showing an example of the binding agent array to which an amplicon has bound. The results show binding to the viral conserved sequence, Y, the human control sequence Z, and the viral strain-specific sequence $X_{16}$.

Each of the binding agents in the array is comprises a microsphere or bead with a distinct size and distinct intensity of fluorescent (TMR) label. Beads comprising diameters of 3.0 μm, 3.5 μm, 3.77 μm, 5.0 μm, 5.6 μm and 6.8 μm may be differentiated from each other using flow cytometry, as shown in FIG. 4.

For each given size of microsphere, a fluorescent label (TMR) was incorporated at relative intensities of 0%, approximately 150-80;1 (medium), and approximately 3:1 (high). These label intensities could be clearly distinguished using flow cytometry.

Example 3

Comparison of the Multiplex Detection Method with Traditional HPV Diagnosis

Table 5, below, provides an overview comparing the multiplex HPV detection method of the present invention with the current histological method for HPV diagnosis.

TABLE 5

Comparison of HPV diagnostic methods

| HPV Diagnostic Method | Throughput | Report | Controls |
|---|---|---|---|
| Present Invention | 1600 per day, per instrument | all 13 "high risk" strains individually identified | internal control, positive control, human gDNA control |
| Histological based method | 350 per day | "high risk" class generally identified | no internal control, "low risk" positive control, "high risk positive control |

Example 4

Sensitivity Testing for Probe Methodology

Figure 8:
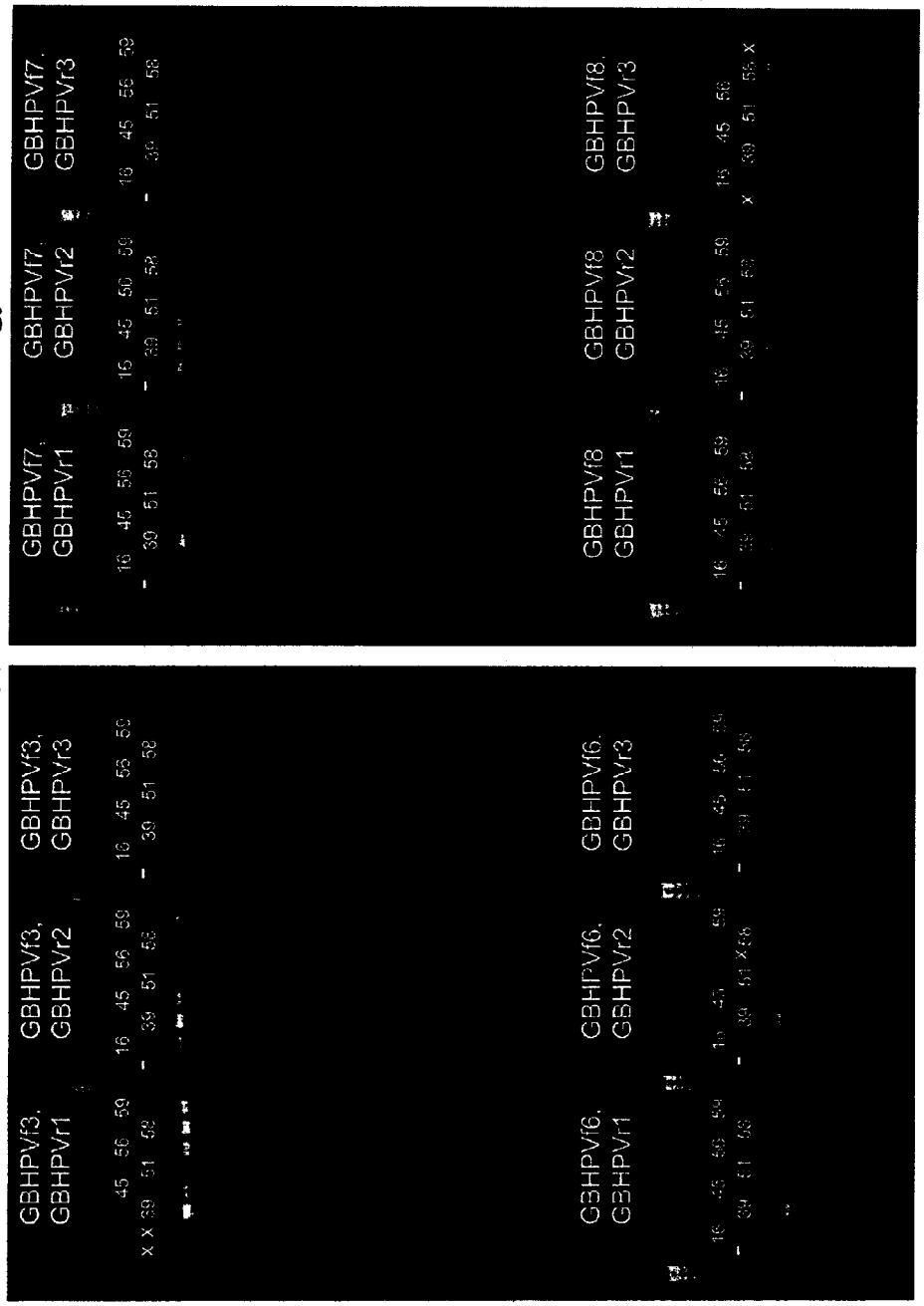
FIG. 8 is a photographical representation showing agarose gel electrophoretic analysis of PCR products following amplification from HPV type-specific insert-containing plasmids using various combinations of primers.

Five microliters of each product was loaded alongside lanes containing 5 microliters of HyperladderIV DNA ladder (FIG. 8). Reactions were templated with 40000 copies of type-specific plasmid (numbers in lanes indicate type) and subjected to 40 amplification cycles using an annealing temperature of 44° C. An 'x' in lanes indicates reactions not analysed due to evaporative loss during PCR. A '-' in lanes indicates no template controls. 200 or 100 copies of type-specific plasmids along with 10 ng of Jurkat human genomic DNA were used to template PCRs employing GBHPVf3+ and GBHPVr1 multiplexed with MLC1_95f and T7aMLC1_275r. Forty-eight amplification cycles were performed using an annealing temperature of 44° C. Analysis was performed by flow cytometry following lambda exonuclease digestion and hybridization to PapType probe beads. No template controls yielded negative results across types. All types tested: 6, 11, 16, 18, 31, 45, 51, 52, 56, 58, 59, 66 and 68 yielded positive results using 200 copies of type-specific plasmids. All above types except types 51 and 59 yielded positive results using 100 copies of type-specific plasmids, indicating a very sensitive and relatively unbiased system.

When ranges are used herein for physical properties, such as temperature or number of nucleotides in a sequence, all combinations and subcombinations of ranges and specific embodiments therein are intended to be included.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any to or more of said steps or features.

BIBLIOGRAPHY

Bonner and Laskey, *Eur. J. Biochem.* 46:83, 1974
Chadwick et al., *J. Virol. Methods* 70:59-70, 1998
Chan and Fox, *Rev. Med. Microbiol.* 10:185-196, 1999
Compton, *Nature* 350:91-92, 1991
Demidov and Broude (Eds.), "*DNA Amplification. Current Technologies and Applications*", Horizon Bioscience, 2004
Guatelli et al., *Proc. Natl. Acad. Sci. USA* 87:1874-1878, 1990
Hill, *J. Clin. Ligand Assay* 19:43-51, 1996
Kievits et al., *J. Virol. Methods* 35:273-286, 1991
Kuske et al., *Appl. Environ. Microbiol.* 64(7):2463-2472, 1998
Lizardi et al., *Biotechnology* 6:1197-1202, 1988
Lyamichev et al., *Nat. Biotechnol.* 17:292-296, 1999
Marmur and Doty, *J. Mol. Biol.* 5:109, 1962
Nelson and Krawetz, *Anal. Biochem.* 207(1):97-201, 1992
Pawlotsky et al., *J. Virol. Methods* 79:227-235, 1999
Ryan et al., *Mol. Diagn.* 4:135-144, 1999
Speel, *Histochem. Cell Biol.* 112:89-113, 1999
Todd et al., *J. AIDS Hum. Retrovirol.* 10:S35-S44, 1995

What is claimed:

1. A forward and reverse primer pair for targeting oncogenic HPV, wherein:
the forward primer of the primer pair is /5Phos/ggaacaatca rytrtttgtt actgtkgtdg a (SEQ ID NO: 36) or SEQ ID NO: 36 wherein the 5' g nucleotide is not phosphorylated; and
the reverse primer of the primer pair is SEQ ID NO: 9, wherein the reverse primer is optionally conjugated to a heel at the 5' terminus of the reverse primer.

2. The primer pair of claim 1, wherein the reverse primer comprises a heel selected from the group consisting of: SEQ ID NO: 87, 88, 89, 91, 92, 93 and 94.

3. The primer pair of claim 1, wherein the reverse primer comprises a heel selected from the group consisting of: SEQ ID NO: 87 and 91, conjugated to the 5' terminus of the reverse primer.

4. A primer set comprising the primer pair of claim 1, further comprising an additional forward primer selected from the group consisting of: SEQ ID NO: 1, 2, 4, 5, 6, 7, and 8; wherein the additional forward primer is optionally conjugated to a heel at the 5' terminus of the additional forward primer.

5. A primer set comprising the primer pair of claim 1, further comprising an additional reverse primer selected from the group consisting of: SEQ ID NO: 10, 11 and 12; wherein the additional reverse primer is optionally conjugated to a heel at the 5' terminus of the additional reverse primer.

6. The primer set of claim 4, wherein said additional forward primer is SEQ ID NO: 8 with a heel sequence that is CTGTT or /5Phos/CTGTT conjugated to the 5' terminus of the additional forward primer.

7. The primer set of claim 5, wherein said additional reverse primer is SEQ ID NO: 11 with a heel sequence that is selected from the group consisting of: SEQ ID NO: 89, SEQ ID NO: 92 or SEQ ID NO: 93 conjugated to the 5' terminus of the additional reverse primer.

8. The primer pair of claim 1, wherein the forward primer is SEQ ID NO: 36 wherein the 5' g nucleotide is not phosphorylated.

9. The primer pair of claim 3, wherein the reverse primer is SEQ ID NO: 9 with a heel sequence that is SEQ ID NO: 87 conjugated to the 5' terminus of the reverse primer.

10. The primer pair of claim 1, wherein the reverse primer comprises a heel sequence that is SEQ ID NO: 90 conjugated to the 5' terminus of the reverse primer.

11. A method for diagnosing HPV infection in a human subject, said method comprising:
(i) obtaining a biological sample from the human subject which putatively comprises HPV;
(ii) isolating nucleic acid from said sample;
(iii) amplifying the nucleic acid from said sample using a primer pair according to claim 1, which generate an amplicon which is distinct for said analyte or a particular strain of said analyte;
(iv) optionally amplifying a control nucleic acid sequence from the genomic DNA of the human subject;
(v) optionally effecting labelling of the amplicon(s) recited at steps (iii) and/or (iv);
(vi) hybridizing the labelled amplicon(s) to a beadset of reactants wherein each member of the beadset comprises a nucleic acid molecule having complementarity to a nucleotide sequence of HPV or a particular strain of HPV or a control nucleotide sequence, bound or otherwise associated with a physiochemically distinguishable substrate; and
(vii) determining to which of the reactants an amplicon has bound; wherein the association of an amplicon with a particular reactant is indicative of HPV infection in the human subject.

12. A method for determining the risk of a human subject developing a disease associated with one or more strains of HPV said method comprising:
(i) obtaining a biological sample from the human subject which putatively comprises HPV;
(ii) isolating nucleic acid from said sample;
(iii) amplifying the nucleic acid from said sample using a primer pair according to claim 1, which generate an amplicon which is distinct for said analyte or a particular strain of said analyte;
(iv) optionally amplifying a control nucleic acid sequence from the genomic DNA of the human subject;
(v) optionally effecting labelling of the amplicon(s) recited at steps (iii) and/or (iv);
(vi) hybridizing the labelled amplicon(s) to a beadset of reactants wherein each member of the beadset comprises a nucleic acid molecule having complementarity to a nucleotide sequence of HPV or a particular strain of HPV or a control nucleotide sequence, bound or otherwise associated with a physiochemically distinguishable substrate; and
(vii) determining to which of the reactants an amplicon has bound; wherein the association of an amplicon with a particular reactant comprising a polynucleotide which is complementary to a strain of HPV associated with a particular disease, is indicative of an increased risk for said disease in the subject.

13. A method for diagnosing HPV infection in a human subject, said method comprising:
(i) obtaining a biological sample from the human subject which putatively comprises HPV;
(ii) isolating nucleic acid from said sample;
(iii) amplifying the nucleic acid from said sample using a primer pair according to claim 1, which generate an amplicon which is distinct for said analyte or a particular strain of said analyte;
(iv) optionally amplifying a control nucleic acid sequence from the genomic DNA of the human subject;
(v) hybridizing the labelled amplicon(s) to a beadset of reactants wherein each member of the beadset comprises a nucleic acid molecule having complementarity to a nucleotide sequence of HPV or a particular strain of HPV or a control nucleotide sequence, bound or otherwise associated with a physiochemically distinguishable substrate and wherein the hybridizing occurs in the presence of at least one signal oligonucleotide sequence; and
(vi) determining to which of the reactants an amplicon has bound; wherein the association of an amplicon with a particular reactant is indicative of HPV infection in the human subject.

14. A method of claim 13, wherein the beadset of reactants comprises a plurality of families or a plurality of subsets of beads having:
(a) at least two subsets of beads, wherein each subset of beads is physiochemically distinguishable from any other bead subset based on at least size; or
(b) at least one subset of beads having at least two families, wherein the beads in a bead subset are homogeneous in size with respect to each other, and are physiochemically distinguishable into two or more families of beads based on the level of labelling each contains, or (c) a combination of said families of beads and said subsets of beads; and wherein:

the beads within each bead family of a subset are each coupled to an optionally-labelled nucleic acid capture probe capable of binding to a HPV strain-specific region of an HPV genome or, optionally, to at least one of a control nucleic acid sequence, provided that any nucleic acid capture probe or control nucleic acid sequence is labelled with the same label as other labelled capture probes or control nucleic acid sequence in the bead subset, and that within any single subset of beads, each family of beads thereof has a different fluorescent intensity; and each family of beads is specific for the detection of a strain of HPV different from any other bead family in the beadset; wherein said beadset is capable of identifying one or more specific strains of HPV through analysis of bead size, fluorescent intensity, or sequence discrimination of the at least one bead family or bead subset, using flow cytometry.

15. A method for determining the risk of a human subject developing a disease associated with one or more strains of HPV said method comprising:
    (i) obtaining a biological sample from the human subject which putatively comprises HPV;
    (ii) isolating nucleic acid from said sample;
    (iii) amplifying the nucleic acid from said sample using a primer pair according to claim 1, which generate an amplicon which is distinct for said analyte or a particular strain of said analyte;
    (iv) optionally amplifying a control nucleic acid sequence from the genomic DNA of the human subject;
    (v) hybridizing the labelled amplicon(s) to a beadset of reactants wherein each member of the beadset comprises a nucleic acid molecule having complementarity to a nucleotide sequence of HPV or a particular strain of HPV or a control nucleotide sequence, bound or otherwise associated with a physiochemically distinguishable substrate and wherein the hybridizing occurs in the presence of at least one signal oligonucleotide sequence; and
    (vi) determining to which of the reactant an amplicon has bound; wherein the association of an amplicon with a particular reactant comprising a polynucleotide which is complementary to a strain of HPV associated with a particular disease, is indicative of an increased risk for said disease in the subject.

16. A method of claim 15, wherein the beadset of reactants comprises a plurality of families or a plurality of subsets of beads having:
    (a) at least two subsets of beads, wherein each subset of beads is physiochemically distinguishable from any other bead subset based on at least size; or
    (b) at least one subset of beads having at least two families, wherein the beads in a bead subset are homogeneous in size with respect to each other, and are physiochemically distinguishable into two or more families of beads based on the level of labelling each contains, or
    (c) a combination of said families of beads and said subsets of beads; and wherein:
    the beads within each bead family of a subset are each coupled to an optionally-labelled nucleic acid capture probe capable of binding to a HPV strain-specific region of an HPV genome or, optionally, to at least one of a control nucleic acid sequence, provided that any nucleic acid capture probe or control nucleic acid sequence is labelled with the same label as other labelled capture probes or control nucleic acid sequence in the bead subset, and that within any single subset of beads, each family of beads thereof has a different fluorescent intensity; and each family of beads is specific for the detection of a strain of HPV different from any other bead family in the beadset; wherein said beadset is capable of identifying one or more specific strains of HPV through analysis of bead size, fluorescent intensity, or sequence discrimination of the at least one bead family or bead subset, using flow cytometry.

17. A method for diagnosing HPV infection in a human subject, said method comprising:
    (i) obtaining a biological sample from the human subject which putatively comprises HPV;
    (ii) isolating nucleic acid from said sample;
    (iii) amplifying the nucleic acid from said sample using a primer pair according to claim 1, which generate an amplicon which is distinct for said analyte or a particular strain of said analyte;
    (iv) optionally amplifying a control nucleic acid sequence from the genomic DNA of the human subject;
    (v) optionally effecting labelling of the amplicon(s) recited at steps (iii) and/or (iv);
    (vi) hybridizing the labelled amplicon(s) to a beadset of reactants wherein each member of the beadset comprises a nucleic acid molecule having complementarity to a nucleotide sequence of HPV or a particular strain of HPV or a control nucleotide sequence, bound or otherwise associated with a physiochemically distinguishable substrate and wherein the hybridizing occurs in the presence of at least one blocking oligonucleotide sequence; and
    (vii) determining to which of the reactants an amplicon has bound; wherein the association of an amplicon with a particular reactant is indicative of HPV infection in the human subject.

18. A method of claim 17, wherein the beadset of reactants comprises a plurality of families or a plurality of subsets of beads having:
    (a) at least two subsets of beads, wherein each subset of beads is physiochemically distinguishable from any other bead subset based on at least size; or
    (b) at least one subset of beads having at least two families, wherein the beads in a bead subset are homogeneous in size with respect to each other, and are physiochemically distinguishable into two or more families of beads based on the level of labelling each contains, or
    (c) a combination of said families of beads and said subsets of beads; and wherein:
    the beads within each bead family of a subset are each coupled to an optionally-labelled nucleic acid capture probe capable of binding to a HPV strain-specific region of an HPV genome or, optionally, to at least one of a control nucleic acid sequence, provided that any nucleic acid capture probe or control nucleic acid sequence is labelled with the same label as other labelled capture probes or control nucleic acid sequence in the bead subset, and that within any single subset of beads, each family of beads thereof has a different fluorescent intensity; and each family of beads is specific for the detection of a strain of HPV different from any other bead family in the beadset; wherein said beadset is capable of identifying one or more specific strains of HPV through analysis of bead size, fluorescent intensity, or sequence discrimination of the at least one bead family or bead subset, using flow cytometry.

19. A method for determining the risk of a human subject developing a disease associated with one or more strains of HPV said method comprising:
(i) obtaining a biological sample from the human subject which putatively comprises HPV;
(ii) isolating nucleic acid from said sample;
(iii) amplifying the nucleic acid from said sample using a primer pair according to claim 1, which generate an amplicon which is distinct for said analyte or a particular strain of said analyte;
(iv) optionally amplifying a control nucleic acid sequence from the genomic DNA of the human subject;
(v) optionally effecting labelling of the amplicon(s) recited at steps (iii) and/or (iv);
(vi) hybridizing the labelled amplicon(s) to a beadset of reactants wherein each member of the beadset comprises a nucleic acid molecule having complementarity to a nucleotide sequence of HPV or a particular strain of HPV or a control nucleotide sequence, bound or otherwise associated with a physiochemically distinguishable substrate and wherein the hybridizing occurs in the presence of at least one blocking oligonucleotide sequence; and
(vii) determining to which of the reactant an amplicon has bound; wherein the association of an amplicon with a particular reactant comprising a polynucleotide which is complementary to a strain of HPV associated with a particular disease, is indicative of an increased risk for said disease in the subject.

20. A method of claim 19, wherein the beadset of reactants comprises a plurality of families or a plurality of subsets of beads having:
(a) at least two subsets of beads, wherein each subset of beads is physiochemically distinguishable from any other bead subset based on at least size; or
(b) at least one subset of beads having at least two families, wherein the beads in a bead subset are homogeneous in size with respect to each other, and are physiochemically distinguishable into two or more families of beads based on the level of labelling each contains, or
(c) a combination of said families of beads and said subsets of beads; and wherein:
the beads within each bead family of a subset are each coupled to an optionally-labelled nucleic acid capture probe capable of binding to a HPV strain-specific region of an HPV genome or, optionally, to at least one of a control nucleic acid sequence, provided that any nucleic acid capture probe or control nucleic acid sequence is labelled with the same label as other labelled capture probes or control nucleic acid sequence in the bead subset, and that within any single subset of beads, each family of beads thereof has a different fluorescent intensity; and
each family of beads is specific for the detection of a strain of HPV different from any other bead family in the beadset; wherein said beadset is capable of identifying one or more specific strains of HPV through analysis of bead size, fluorescent intensity, or sequence discrimination of the at least one bead family or bead subset, using flow cytometry.

21. A method for diagnosing HPV infection in a human subject, said method comprising:
(i) obtaining a biological sample from the human subject which putatively comprises HPV;
(ii) isolating nucleic acid from said sample;
(iii) amplifying the nucleic acid from said sample using a primer pair according to claim 1, which generate an amplicon which is distinct for said analyte or a particular strain of said analyte;
(iv) optionally amplifying a control nucleic acid sequence from the genomic DNA of the human subject;
(v) hybridizing the labelled amplicon(s) to a beadset of reactants wherein each member of the beadset comprises a nucleic acid molecule having complementarity to a nucleotide sequence of HPV or a particular strain of HPV or a control nucleotide sequence, bound or otherwise associated with a physiochemically distinguishable substrate and wherein the hybridizing occurs in the presence of at least one signal oligonucleotide sequence and at least one blocking oligonucleotide sequence; and
(vi) determining to which of the reactants an amplicon has bound; wherein the association of an amplicon with a particular reactant is indicative of HPV infection in the human subject.

22. A method of claim 13, wherein the beadset of reactants comprise a plurality of families or a plurality of subsets of beads having:
(a) at least two subsets of beads, wherein each subset of beads is physiochemically distinguishable from any other bead subset based on at least size; or
(b) at least one subset of beads having at least two families, wherein the beads in a bead subset are homogeneous in size with respect to each other, and are physiochemically distinguishable into two or more families of beads based on the level of labelling each contains, or
(c) a combination of said families of beads and said subsets of beads; and wherein:
the beads within each bead family of a subset are each coupled to an optionally-labelled nucleic acid capture probe capable of binding to a HPV strain-specific region of an HPV genome or, optionally, to at least one of a control nucleic acid sequence, provided that any nucleic acid capture probe or control nucleic acid sequence is labelled with the same label as other labelled capture probes or control nucleic acid sequence in the bead subset, and that within any single subset of beads, each family of beads thereof has a different fluorescent intensity; and
each family of beads is specific for the detection of a strain of HPV different from any other bead family in the beadset; wherein said beadset is capable of identifying one or more specific strains of HPV through analysis of bead size, fluorescent intensity, or sequence discrimination of the at least one bead family or bead subset, using flow cytometry.

23. A method for determining the risk of a human subject developing a disease associated with one or more strains of HPV said method comprising:
(i) obtaining a biological sample from the human subject which putatively comprises HPV;
(ii) isolating nucleic acid from said sample;
(iii) amplifying the nucleic acid from said sample using a primer pair according to claim 1, which generate an amplicon which is distinct for said analyte or a particular strain of said analyte;
(iv) optionally amplifying a control nucleic acid sequence from the genomic DNA of the human subject;
(v) hybridizing the labelled amplicon(s) to a beadset of reactants wherein each member of the beadset comprises a nucleic acid molecule having complementarity to a nucleotide sequence of HPV or a particular strain of HPV or a control nucleotide sequence, bound or otherwise associated with a physiochemically distinguishable substrate and wherein the hybridizing occurs in the presence of at least one signal oligonucleotide sequence and at least one blocking oligonucleotide sequence; and
(vi) determining to which of the reactant an amplicon has bound; wherein the association of an amplicon with a particular reactant comprising a polynucleotide which is complementary to a strain of HPV associated with a particular disease, is indicative of an increased risk for said disease in the subject.

24. A method of claim 13, wherein the beadset of reactants comprises a plurality of families or a plurality of subsets of beads having:
(a) at least two subsets of beads, wherein each subset of beads is physiochemically distinguishable from any other bead subset based on at least size; or
(b) at least one subset of beads having at least two families, wherein the beads in a bead subset are homogeneous in size with respect to each other, and are physiochemically distinguishable into two or more families of beads based on the level of labelling each contains, or
(c) a combination of said families of beads and said subsets of beads; and wherein:
the beads within each bead family of a subset are each coupled to an optionally-labelled nucleic acid capture probe capable of binding to a HPV strain-specific region of an HPV genome or, optionally, to at least one of a control nucleic acid sequence, provided that any nucleic acid capture probe or control nucleic acid sequence is labelled with the same label as other labelled capture probes or control nucleic acid sequence in the bead subset, and that within any single subset of beads, each family of beads thereof has a different fluorescent intensity; and
each family of beads is specific for the detection of a strain of HPV different from any other bead family in the beadset; wherein said beadset is capable of identifying one or more specific strains of HPV through analysis of bead size, fluorescent intensity, or sequence discrimination of the at least one bead family or bead subset, using flow cytometry.

* * * * *

SEQUENCE LISTING

<160> NUMBER OF SEQ ID NOS: 108

<210> SEQ ID NO 1
<211> LENGTH: 24
<212> TYPE: DNA
<213> ORGANISM: Artificial
<220> FEATURE:
<223> OTHER INFORMATION: Synthetic primer

<400> SEQUENCE: 1
trtttgttac tgtkgtdgat acya                                              24

<210> SEQ ID NO 2
<211> LENGTH: 25
<212> TYPE: DNA
<213> ORGANISM: Artificial
<220> FEATURE:
<223> OTHER INFORMATION: Synthetic primer

<400> SEQUENCE: 2
carytrtttg ttactgtkgt dgata                                             25

<210> SEQ ID NO 3
<211> LENGTH: 23
<212> TYPE: DNA
<213> ORGANISM: Artificial
<220> FEATURE:
<223> OTHER INFORMATION: Synthetic primer

<400> SEQUENCE: 3
carytrtttg ttactgtkgt dga                                               23

<210> SEQ ID NO 4
<211> LENGTH: 23
<212> TYPE: DNA
<213> ORGANISM: Artificial
<220> FEATURE:
<223> OTHER INFORMATION: Synthetic primer

<400> SEQUENCE: 4
aaycarytrt ttgttactgt kgt                                               23

<210> SEQ ID NO 5
<211> LENGTH: 26
<212> TYPE: DNA
<213> ORGANISM: Artificial
<220> FEATURE:
<223> OTHER INFORMATION: Synthetic primer

<400> SEQUENCE: 5
tttgttactg tkgtdgatac yachcg                                            26

<210> SEQ ID NO 6
<211> LENGTH: 29
<212> TYPE: DNA
<213> ORGANISM: Artificial
<220> FEATURE:
<223> OTHER INFORMATION: Synthetic primer

<400> SEQUENCE: 6
tttgttactg tkgtdgatac yachcgyag                                         29

<210> SEQ ID NO 7
<211> LENGTH: 23
<212> TYPE: DNA

```
<213> ORGANISM: Artificial
<220> FEATURE:
<223> OTHER INFORMATION: Synthetic primer

<400> SEQUENCE: 7
gtkgtdgata cyachcgyag tac                                          23

<210> SEQ ID NO 8
<211> LENGTH: 23
<212> TYPE: DNA
<213> ORGANISM: Artificial
<220> FEATURE:
<223> OTHER INFORMATION: Synthetic primer

<400> SEQUENCE: 8
gtdgatacya chcgyagtac haa                                          23

<210> SEQ ID NO 9
<211> LENGTH: 35
<212> TYPE: DNA
<213> ORGANISM: Artificial
<220> FEATURE:
<223> OTHER INFORMATION: Synthetic primer

<400> SEQUENCE: 9
tgaaaaataa aytgyaaatc atattcytcm mcatg                             35

<210> SEQ ID NO 10
<211> LENGTH: 26
<212> TYPE: DNA
<213> ORGANISM: Artificial
<220> FEATURE:
<223> OTHER INFORMATION: Synthetic primer

<400> SEQUENCE: 10
cayarytgaa aaataaaytg yaaatc                                       26

<210> SEQ ID NO 11
<211> LENGTH: 22
<212> TYPE: DNA
<213> ORGANISM: Artificial
<220> FEATURE:
<223> OTHER INFORMATION: Synthetic primer

<400> SEQUENCE: 11
trcayarytg aaaaataaay tg                                           22

<210> SEQ ID NO 12
<211> LENGTH: 19
<212> TYPE: DNA
<213> ORGANISM: Artificial
<220> FEATURE:
<223> OTHER INFORMATION: Synthetic primer

<400> SEQUENCE: 12
trcayarytg aaaaataaa                                               19

<210> SEQ ID NO 13
<211> LENGTH: 23
<212> TYPE: DNA
<213> ORGANISM: Artificial
<220> FEATURE:
<223> OTHER INFORMATION: Synthetic primer

<400> SEQUENCE: 13
tttgttactg tggtagatac tac                                          23
```

```
<210> SEQ ID NO 14
<211> LENGTH: 25
<212> TYPE: DNA
<213> ORGANISM: Artificial
<220> FEATURE:
<223> OTHER INFORMATION: Synthetic primer

<400> SEQUENCE: 14
gaaaaataaa ctgtaaatca tattc                                            25

<210> SEQ ID NO 15
<211> LENGTH: 23
<212> TYPE: DNA
<213> ORGANISM: Artificial
<220> FEATURE:
<223> OTHER INFORMATION: Synthetic primer

<400> SEQUENCE: 15
tttkttachg tkgtdgatac yac                                              23

<210> SEQ ID NO 16
<211> LENGTH: 25
<212> TYPE: DNA
<213> ORGANISM: Artificial
<220> FEATURE:
<223> OTHER INFORMATION: Synthetic primer

<400> SEQUENCE: 16
gaaahataaa ytgyaadtca taytc                                            25

<210> SEQ ID NO 17
<211> LENGTH: 23
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5Phos-T

<400> SEQUENCE: 17
tttgttactg tggtagatac tac                                              23

<210> SEQ ID NO 18
<211> LENGTH: 25
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5AmMc6-G

<400> SEQUENCE: 18
gaaaaataaa ctgtaaatca tattc                                            25

<210> SEQ ID NO 19
<211> LENGTH: 23
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5Phos-T
```

-continued

```
<400> SEQUENCE: 19
tttkttachg tkgtdgatac yac                                            23

<210> SEQ ID NO 20
<211> LENGTH: 25
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5AmMC6-G

<400> SEQUENCE: 20
gaaahataaa ytgyaadtca taytc                                          25

<210> SEQ ID NO 21
<211> LENGTH: 23
<212> TYPE: DNA
<213> ORGANISM: Artificial
<220> FEATURE:
<223> OTHER INFORMATION: Synthetic primer

<400> SEQUENCE: 21
tttkttachg tkgtdgatac hac                                            23

<210> SEQ ID NO 22
<211> LENGTH: 50
<212> TYPE: DNA
<213> ORGANISM: Artificial
<220> FEATURE:
<223> OTHER INFORMATION: Synthetic primer

<400> SEQUENCE: 22
aattctaata cgactcacta gggggaaah ataaaytgya adtcataytc                 50

<210> SEQ ID NO 23
<211> LENGTH: 23
<212> TYPE: DNA
<213> ORGANISM: Artificial
<220> FEATURE:
<223> OTHER INFORMATION: Synthetic primer

<400> SEQUENCE: 23
tttkttachg tdgtdgayac hac                                            23

<210> SEQ ID NO 24
<211> LENGTH: 50
<212> TYPE: DNA
<213> ORGANISM: Artificial
<220> FEATURE:
<223> OTHER INFORMATION: Synthetic primer

<400> SEQUENCE: 24
aattctaata cgactcacta gggggaaah ataaaytgya rdtcawaytc                 50

<210> SEQ ID NO 25
<211> LENGTH: 23
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5Phos-T
```

```
<400> SEQUENCE: 25
tttkttachg tkgtdgatac hac                                           23

<210> SEQ ID NO 26
<211> LENGTH: 50
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5AmMC6-A

<400> SEQUENCE: 26
aattctaata cgactcacta tagggaaah ataaaytgya adtcataytc               50

<210> SEQ ID NO 27
<211> LENGTH: 23
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5Phos-T

<400> SEQUENCE: 27
tttgttachg tdgtdgayac hac                                           23

<210> SEQ ID NO 28
<211> LENGTH: 50
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5AmMC6-A

<400> SEQUENCE: 28
aattctaata cgactcacta tagggaaah ataaaytgya rdtcawaytc               50

<210> SEQ ID NO 29
<211> LENGTH: 18
<212> TYPE: DNA
<213> ORGANISM: Artificial
<220> FEATURE:
<223> OTHER INFORMATION: Synthetic primer

<400> SEQUENCE: 29
ggcacccaga caatacac                                                 18

<210> SEQ ID NO 30
<211> LENGTH: 45
<212> TYPE: DNA
<213> ORGANISM: Artificial
<220> FEATURE:
<223> OTHER INFORMATION: Synthetic primer

<400> SEQUENCE: 30
aattctaata cgactcacta tagggtaagt tgaagaggtg aagaa                   45

<210> SEQ ID NO 31
<211> LENGTH: 18
<212> TYPE: DNA
```

```
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5Phos-G

<400> SEQUENCE: 31
ggcacccaga caatacac                                                   18

<210> SEQ ID NO 32
<211> LENGTH: 45
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5AmMC6-A

<400> SEQUENCE: 32
aattctaata cgactcacta tagggtaagt tgaagaggtg aagaa                     45

<210> SEQ ID NO 33
<211> LENGTH: 32
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5Phos-C

<400> SEQUENCE: 33
caatcagctr tttgttactg tkgtdgatac ya                                   32

<210> SEQ ID NO 34
<211> LENGTH: 30
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5Phos-A

<400> SEQUENCE: 34
acaatcaryt rtttgttact gtkgtdgata                                      30

<210> SEQ ID NO 35
<211> LENGTH: 28
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5Phos-A

<400> SEQUENCE: 35
acaatcaryt rtttgttact gtkgtdga                                        28

<210> SEQ ID NO 36
<211> LENGTH: 31
<212> TYPE: DNA
```

```
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5Phos-G

<400> SEQUENCE: 36
ggaacaatca rytrtttgtt actgtkgtdg a                            31

<210> SEQ ID NO 37
<211> LENGTH: 28
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5Phos-G

<400> SEQUENCE: 37
ggaacaayca rytrtttgtt actgtkgt                                28

<210> SEQ ID NO 38
<211> LENGTH: 32
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5Phos-C

<400> SEQUENCE: 38 cagcttttg ttactgtkgt dgatacyach cg                            32

<210> SEQ ID NO 39
<211> LENGTH: 35
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5Phos-C

<400> SEQUENCE: 39 cagcttttg ttactgtkgt dgatacyach cgyag                         35

<210> SEQ ID NO 40
<211> LENGTH: 29
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5Phos-A

<400> SEQUENCE: 40
attaccgtkg tdgatacyac hcgyagtac                               29

<210> SEQ ID NO 41
<211> LENGTH: 28
<212> TYPE: DNA
```

-continued

```
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5Phos-C

<400> SEQUENCE: 41
ctgttgtdga tacyachcgy agtachaa                                              28

<210> SEQ ID NO 42
<211> LENGTH: 47
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5AmMC6-A

<400> SEQUENCE: 42
actcactata ggtgaaaaat aaaytgyaaa tcatattcyt cmmcatg                          47

<210> SEQ ID NO 43
<211> LENGTH: 44
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5AmMC6-A

<400> SEQUENCE: 43
aatacgactc actataggca yarytgaaaa ataaaytgya aatc                             44

<210> SEQ ID NO 44
<211> LENGTH: 43
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5AmMC6-T

<400> SEQUENCE: 44
tctaatacga ctcactatag gtrcayaryt gaaaaataaa ytg                              43

<210> SEQ ID NO 45
<211> LENGTH: 43
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5AmMC6-A

<400> SEQUENCE: 45
aattctaata cgactcacta taggtrcaya rytgaaaaat aaa                              43

<210> SEQ ID NO 46
<211> LENGTH: 51
<212> TYPE: DNA
```

```
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 46
aaagggagga cagctatgga catccgtaac tacatcttcc acatacacca a          51

<210> SEQ ID NO 47
<211> LENGTH: 51
<212> TYPE: DNA
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 47
aaagggagga cagctatgga catctgtgtc taaatctgct acatacacta a          51

<210> SEQ ID NO 48
<211> LENGTH: 51
<212> TYPE: DNA
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 48
aaagggagga cagctatgga cgtcattatg tgctgccata tctacttcag a          51

<210> SEQ ID NO 49
<211> LENGTH: 51
<212> TYPE: DNA
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 49
aaagggagga cagctatgga cctcctgtac ctgggcaata tgatgctacc a          51

<210> SEQ ID NO 50
<211> LENGTH: 51
<212> TYPE: DNA
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 50
aaagggagga cagctatgga ctgtttgtgc tgcaattgca aacagtgata c          51

<210> SEQ ID NO 51
<211> LENGTH: 51
<212> TYPE: DNA
```

```
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 51
aaagggagga cagctatgga ctttatgcac acaagtaact agtgacagta c         51

<210> SEQ ID NO 52
<211> LENGTH: 51
<212> TYPE: DNA
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 52
aaagggagga cagctatgga cgtctgtgtg ttctgctgtg tcttctagtg a         51

<210> SEQ ID NO 53
<211> LENGTH: 51
<212> TYPE: DNA
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 53
aaagggagga cagctatgga ctctacctct atagagtctt ccataccttc t         51

<210> SEQ ID NO 54
<211> LENGTH: 51
<212> TYPE: DNA
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 54
aaagggagga cagctatgga cacacaaaat cctgtgccaa gtacatatga c         51

<210> SEQ ID NO 55
<211> LENGTH: 51
<212> TYPE: DNA
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 55
aaagggagga cagctatgga cagcactgcc actgctgcgg tttccccaac a         51

<210> SEQ ID NO 56
<211> LENGTH: 51
<212> TYPE: DNA
```

```
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 56
aaagggagga cagctatgga ctgctgaggt taaaaggaa agcacatata a        51

<210> SEQ ID NO 57
<211> LENGTH: 51
<212> TYPE: DNA
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 57
aaagggagga cagctatgga cgtactgcta cagaacagtt aagtaaatat g        51

<210> SEQ ID NO 58
<211> LENGTH: 46
<212> TYPE: DNA
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 58
aaagggagga cagctatgga cgcactgaag taactaagga aggtac              46

<210> SEQ ID NO 59
<211> LENGTH: 51
<212> TYPE: DNA
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 59
aaagggagga cagctatgga ctctactact tcttctattc ctaatgtata c        51

<210> SEQ ID NO 60
<211> LENGTH: 51
<212> TYPE: DNA
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 60
aaagggagga cagctatgga ctattaatgc agctaaaagc acattaacta a        51

<210> SEQ ID NO 61
<211> LENGTH: 51
<212> TYPE: DNA
```

-continued

```
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 61
aaagggagga cagctatgga ctctactact actgaatcag ctgtaccaaa t         51

<210> SEQ ID NO 62
<211> LENGTH: 48
<212> TYPE: DNA
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 62
aaagggagga cagctatgga ctccactact acagactcta ctgtacca             48

<210> SEQ ID NO 63
<211> LENGTH: 51
<212> TYPE: DNA
<213> ORGANISM: Artificial
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 5Acryd/AAT/iAmMC6T-A

<400> SEQUENCE: 63
aaagggagga cagctatgga ccaaacacag acacagagag acccacagac a         51

<210> SEQ ID NO 64
<211> LENGTH: 30
<212> TYPE: DNA
<213> ORGANISM: Artificial
<220> FEATURE:
<223> OTHER INFORMATION: Synthetic oligonucleotide

<400> SEQUENCE: 64
ttggtctatg tcgaagaagt agtaacggat                                 30

<210> SEQ ID NO 65
<211> LENGTH: 30
<212> TYPE: DNA
<213> ORGANISM: Artificial
<220> FEATURE:
<223> OTHER INFORMATION: Synthetic oligonucleotide

<400> SEQUENCE: 65
ttagtctatg ttgcagaatt agagacagat                                 30

<210> SEQ ID NO 66
<211> LENGTH: 30
<212> TYPE: DNA
<213> ORGANISM: Artificial
<220> FEATURE:
<223> OTHER INFORMATION: Synthetic oligonucleotide

<400> SEQUENCE: 66
tctgatgtag aaatggctgc acaaaatgac                                 30
```

-continued

<210> SEQ ID NO 67
<211> LENGTH: 30
<212> TYPE: DNA
<213> ORGANISM: Artificial
<220> FEATURE:
<223> OTHER INFORMATION: Synthetic oligonucleotide

<400> SEQUENCE: 67
tggtaccatc aaattgcgca ggttcaggag                                    30

<210> SEQ ID NO 68
<211> LENGTH: 30
<212> TYPE: DNA
<213> ORGANISM: Artificial
<220> FEATURE:
<223> OTHER INFORMATION: Synthetic oligonucleotide

<400> SEQUENCE: 68
gtatctctgt tagcaatagc agctgaaaca                                    30

<210> SEQ ID NO 69
<211> LENGTH: 30
<212> TYPE: DNA
<213> ORGANISM: Artificial
<220> FEATURE:
<223> OTHER INFORMATION: Synthetic oligonucleotide

<400> SEQUENCE: 69
gtactctcac ttgttacatg tgtccataaa                                    30

<210> SEQ ID NO 70
<211> LENGTH: 30
<212> TYPE: DNA
<213> ORGANISM: Artificial
<220> FEATURE:
<223> OTHER INFORMATION: Synthetic oligonucleotide

<400> SEQUENCE: 70
tcacttgaag agacagctga acagacagac                                    30

<210> SEQ ID NO 71
<211> LENGTH: 30
<212> TYPE: DNA
<213> ORGANISM: Artificial
<220> FEATURE:
<223> OTHER INFORMATION: Synthetic oligonucleotide

<400> SEQUENCE: 71
agaagctatg gtagactgta tagtggtaga                                    30

<210> SEQ ID NO 72
<211> LENGTH: 30
<212> TYPE: DNA
<213> ORGANISM: Artificial
<220> FEATURE:
<223> OTHER INFORMATION: Synthetic oligonucleotide

<400> SEQUENCE: 72
gtcatttgta catggcagag gatattgtgt                                    30

<210> SEQ ID NO 73
<211> LENGTH: 30
<212> TYPE: DNA
<213> ORGANISM: Artificial
<220> FEATURE:
<223> OTHER INFORMATION: Synthetic oligonucleotide

<400> SEQUENCE: 73
tgttgcggaa agcgcaggag tgggagtgct                                    30

<210> SEQ ID NO 74
<211> LENGTH: 30
<212> TYPE: DNA
<213> ORGANISM: Artificial
<220> FEATURE:
<223> OTHER INFORMATION: Synthetic oligonucleotide

<400> SEQUENCE: 74
ttataagtgc tatccttatt aacgtcagca                                    30

<210> SEQ ID NO 75
<211> LENGTH: 30
<212> TYPE: DNA
<213> ORGANISM: Artificial
<220> FEATURE:
<223> OTHER INFORMATION: Synthetic oligonucleotide

<400> SEQUENCE: 75
catatatact ttactgtact gtaccagtac                                    30

<210> SEQ ID NO 76
<211> LENGTH: 24
<212> TYPE: DNA
<213> ORGANISM: Artificial
<220> FEATURE:
<223> OTHER INFORMATION: Synthetic oligonucleotide

<400> SEQUENCE: 76
taccatcctt tgttacatca gtcc                                          24

<210> SEQ ID NO 77
<211> LENGTH: 30
<212> TYPE: DNA
<213> ORGANISM: Artificial
<220> FEATURE:
<223> OTHER INFORMATION: Synthetic oligonucleotide

<400> SEQUENCE: 77
gtatagatta gcaatagtag aagaagtaga                                    30

<210> SEQ ID NO 78
<211> LENGTH: 30
<212> TYPE: DNA
<213> ORGANISM: Artificial
<220> FEATURE:
<223> OTHER INFORMATION: Synthetic oligonucleotide

<400> SEQUENCE: 78
ttagtaaatg tcctttttgc tgctttaata                                    30

<210> SEQ ID NO 79
<211> LENGTH: 30
<212> TYPE: DNA
<213> ORGANISM: Artificial
<220> FEATURE:
<223> OTHER INFORMATION: Synthetic oligonucleotide

<400> SEQUENCE: 79
atttgctaca ggtgattgag tagaagtaga                                    30

<210> SEQ ID NO 80
<211> LENGTH: 27
<212> TYPE: DNA

```
<213> ORGANISM: Artificial
<220> FEATURE:
<223> OTHER INFORMATION: Synthetic oligonucleotide

<400> SEQUENCE: 80
tggtagagta gtgtctgaag tagagga                                           27

<210> SEQ ID NO 81
<211> LENGTH: 30
<212> TYPE: DNA
<213> ORGANISM: Artificial
<220> FEATURE:
<223> OTHER INFORMATION: Synthetic oligonucleotide

<400> SEQUENCE: 81
tgtctctggg tgtctctctg tctctgtttg                                        30

<210> SEQ ID NO 82
<211> LENGTH: 23
<212> TYPE: DNA
<213> ORGANISM: Artificial
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 5AmMC6-T
<220> FEATURE:
<221> NAME/KEY: modified_base
<222> LOCATION: (23)..(23)
<223> OTHER INFORMATION: A-3Phos

<400> SEQUENCE: 82 tttttttcatg kkgargarta tga                                              23

<210> SEQ ID NO 83
<211> LENGTH: 21
<212> TYPE: DNA
<213> ORGANISM: Artificial
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 5AmMC6-T
<220> FEATURE:
<221> NAME/KEY: modified_base
<222> LOCATION: (21)..(21)
<223> OTHER INFORMATION: T-3Phos

<400> SEQUENCE: 83 tttttttcatg kkgargarta t                                                21

<210> SEQ ID NO 84
<211> LENGTH: 21
<212> TYPE: DNA
<213> ORGANISM: Artificial
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 5AmMC6-T
<220> FEATURE:
<221> NAME/KEY: modified_base
<222> LOCATION: (21)..(21)
<223> OTHER INFORMATION: C-3Phos

<400> SEQUENCE: 84 tttttttacag acacagacaa c                                                21
```

```
<210> SEQ ID NO 85
<211> LENGTH: 22
<212> TYPE: DNA
<213> ORGANISM: Artificial
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 5AmMC6-T
<220> FEATURE:
<221> NAME/KEY: modified_base
<222> LOCATION: (22)..(22)
<223> OTHER INFORMATION: A-3Phos

<400> SEQUENCE: 85 tttttttacag acacagacaa ca                                          22

<210> SEQ ID NO 86
<211> LENGTH: 23
<212> TYPE: DNA
<213> ORGANISM: Artificial
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 5AmMC6-T
<220> FEATURE:
<221> NAME/KEY: modified_base
<222> LOCATION: (23)..(23)
<223> OTHER INFORMATION: C-3Phos

<400> SEQUENCE: 86 tttttttacag acacagacaa cac                                         23

<210> SEQ ID NO 87
<211> LENGTH: 12
<212> TYPE: DNA
<213> ORGANISM: Artificial
<220> FEATURE:
<223> OTHER INFORMATION: Synthetic primer

<400> SEQUENCE: 87
actcactata gg                                                      12

<210> SEQ ID NO 88
<211> LENGTH: 18
<212> TYPE: DNA
<213> ORGANISM: Artificial
<220> FEATURE:
<223> OTHER INFORMATION: Synthetic primer

<400> SEQUENCE: 88
aatacgactc actatagg                                                18

<210> SEQ ID NO 89
<211> LENGTH: 21
<212> TYPE: DNA
<213> ORGANISM: Artificial
<220> FEATURE:
<223> OTHER INFORMATION: Synthetic primer

<400> SEQUENCE: 89
tctaatacga ctcactatag g                                            21

<210> SEQ ID NO 90
<211> LENGTH: 24
<212> TYPE: DNA
```

<213> ORGANISM: Artificial
<220> FEATURE:
<223> OTHER INFORMATION: Synthetic primer

<400> SEQUENCE: 90
aattctaata cgactcacta tagg                                          24

<210> SEQ ID NO 91
<211> LENGTH: 12
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5AmMC6-A

<400> SEQUENCE: 91
actcactata gg                                                       12

<210> SEQ ID NO 92
<211> LENGTH: 18
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5AmMC6-A

<400> SEQUENCE: 92
aatacgactc actatagg                                                 18

<210> SEQ ID NO 93
<211> LENGTH: 21
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5AmMC6-T

<400> SEQUENCE: 93
tctaatacga ctcactatag g                                             21

<210> SEQ ID NO 94
<211> LENGTH: 24
<212> TYPE: DNA
<213> ORGANISM: Artificial
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: 5AmMC6-A

<400> SEQUENCE: 94
aattctaata cgactcacta tagg                                          24

<210> SEQ ID NO 95
<211> LENGTH: 25
<212> TYPE: DNA
<213> ORGANISM: Artificial
<220> FEATURE:
<223> OTHER INFORMATION: Synthetic oligonucleotide

<400> SEQUENCE: 95
aattctaata cgactcacta taggg                                              25

<210> SEQ ID NO 96
<211> LENGTH: 17
<212> TYPE: DNA
<213> ORGANISM: Artificial
<220> FEATURE:
<223> OTHER INFORMATION: Synthetic primer

<400> SEQUENCE: 96
gttttcccag tcacgac                                                       17

<210> SEQ ID NO 97
<211> LENGTH: 17
<212> TYPE: DNA
<213> ORGANISM: Artificial
<220> FEATURE:
<223> OTHER INFORMATION: Synthetic primer

<400> SEQUENCE: 97
gtaaaacgac ggccagt                                                       17

<210> SEQ ID NO 98
<211> LENGTH: 17
<212> TYPE: DNA
<213> ORGANISM: Artificial
<220> FEATURE:
<223> OTHER INFORMATION: Synthetic primer

<400> SEQUENCE: 98
caggaaacag ctatgac                                                       17

<210> SEQ ID NO 99
<211> LENGTH: 22
<212> TYPE: DNA
<213> ORGANISM: Artificial
<220> FEATURE:
<223> OTHER INFORMATION: Synthetic primer

<400> SEQUENCE: 99
gccagggttt tcccagtcac ga                                                 22

<210> SEQ ID NO 100
<211> LENGTH: 24
<212> TYPE: DNA
<213> ORGANISM: Artificial
<220> FEATURE:
<223> OTHER INFORMATION: Synthetic primer

<400> SEQUENCE: 100
gagcggataa caatttcaca cagg                                               24

<210> SEQ ID NO 101
<211> LENGTH: 18
<212> TYPE: DNA
<213> ORGANISM: Artificial
<220> FEATURE:
<223> OTHER INFORMATION: Synthetic primer

<400> SEQUENCE: 101
atttaggtga cactatag                                                      18

<210> SEQ ID NO 102
<211> LENGTH: 24
<212> TYPE: DNA

<213> ORGANISM: Artificial
<220> FEATURE:
<223> OTHER INFORMATION: Synthetic primer

<400> SEQUENCE: 102
catacgattt aggtgacact atag    24

<210> SEQ ID NO 103
<211> LENGTH: 20
<212> TYPE: DNA
<213> ORGANISM: Artificial
<220> FEATURE:
<223> OTHER INFORMATION: Synthetic primer

<400> SEQUENCE: 103
taatacgact cactataggg    20

<210> SEQ ID NO 104
<211> LENGTH: 17
<212> TYPE: DNA
<213> ORGANISM: Artificial
<220> FEATURE:
<223> OTHER INFORMATION: Synthetic primer

<400> SEQUENCE: 104
attaaccctc actaaag    17

<210> SEQ ID NO 105
<211> LENGTH: 24
<212> TYPE: DNA
<213> ORGANISM: Artificial
<220> FEATURE:
<223> OTHER INFORMATION: Synthetic primer

<400> SEQUENCE: 105
gcgcgaaatt aaccctcact aaag    24

<210> SEQ ID NO 106
<211> LENGTH: 20
<212> TYPE: DNA
<213> ORGANISM: Artificial
<220> FEATURE:
<223> OTHER INFORMATION: Synthetic primer

<400> SEQUENCE: 106
tacacacagg tgtacacaga    20

<210> SEQ ID NO 107
<211> LENGTH: 20
<212> TYPE: DNA
<213> ORGANISM: Artificial
<220> FEATURE:
<223> OTHER INFORMATION: Synthetic primer

<400> SEQUENCE: 107
accaagtact ctacgtgttg    20

<210> SEQ ID NO 108
<211> LENGTH: 17
<212> TYPE: DNA
<213> ORGANISM: Artificial
<220> FEATURE:
<223> OTHER INFORMATION: Synthetic primer

<400> SEQUENCE: 108
ggcacccaga catacac    17